(12) United States Patent
Soltani et al.

(10) Patent No.: US 8,192,363 B2
(45) Date of Patent: Jun. 5, 2012

(54) CATHETER WITH MULTIPLE ULTRASOUND RADIATING MEMBERS

(75) Inventors: Azita Soltani, Snohomish, WA (US); Robert L. Wilcox, Bothell, WA (US)

(73) Assignee: EKOS Corporation, Bothell, WA (US)

( * ) Notice: Subject to any disclaimer, the term of this patent is extended or adjusted under 35 U.S.C. 154(b) by 358 days.

(21) Appl. No.: 11/924,482

(22) Filed: Oct. 25, 2007

(65) Prior Publication Data

US 2008/0103417 A1 May 1, 2008

Related U.S. Application Data

(60) Provisional application No. 60/855,172, filed on Oct. 27, 2006.

(51) Int. Cl.
*A61B 8/00* (2006.01)

(52) U.S. Cl. .................. 600/439; 600/459

(58) Field of Classification Search .......... 600/437–469; 601/1–3; 604/22
See application file for complete search history.

(56) References Cited

U.S. PATENT DOCUMENTS

| | | |
|---|---|---|
| 3,430,625 A | 3/1969 | McLeod, Jr. |
| 3,433,226 A | 3/1969 | Boyd |
| 3,565,062 A | 2/1971 | Kuris |
| 3,827,115 A | 8/1974 | Bom |
| 3,941,122 A | 3/1976 | Jones |
| 4,040,414 A | 8/1977 | Suroff |
| 4,192,294 A | 3/1980 | Gekhman et al. |
| 4,309,989 A | 1/1982 | Fahim |
| 4,319,580 A | 3/1982 | Colley et al. |
| 4,354,502 A | 10/1982 | Colley et al. |
| 4,531,943 A | 7/1985 | Van Tassel et al. |
| 4,549,533 A | 10/1985 | Cain et al. |
| 4,587,975 A | 5/1986 | Salo et al. |
| 4,709,698 A | 12/1987 | Johnston et al. |
| 4,750,902 A | 6/1988 | Wuchinich et al. |
| 4,754,752 A | 7/1988 | Ginsburg et al. |
| 4,808,153 A | 2/1989 | Parisi |
| 4,821,740 A | 4/1989 | Tachibana |
| 4,870,953 A | 10/1989 | Michael et al. |
| 4,920,954 A | 5/1990 | Alliger et al. |
| 4,921,478 A | 5/1990 | Solano et al. |
| 4,924,863 A | 5/1990 | Sterzer |
| 4,936,281 A | 6/1990 | Stasz |
| 4,948,587 A | 8/1990 | Kost et al. |
| 4,951,677 A | 8/1990 | Crowley et al. |
| 4,953,565 A | 9/1990 | Tachibana et al. |

(Continued)

FOREIGN PATENT DOCUMENTS

DE 4005743 8/1991

(Continued)

OTHER PUBLICATIONS

International Search Report Application No. PCT/US2007/082724.

(Continued)

*Primary Examiner* — Sanjay Cattungal
(74) *Attorney, Agent, or Firm* — Knobbe, Martens, Olson & Bear, LLP

(57) ABSTRACT

A catheter system for delivering ultrasonic energy to a treatment site includes a tubular body having a proximal end, a distal end and a treatment zone located between the distal end and the proximal end. An ultrasonic assembly is positioned within the treatment zone and provides providing an average longitudinal power density between about 0.2 and about 1.0 W/cm within the treatment zone.

16 Claims, 17 Drawing Sheets

U.S. PATENT DOCUMENTS

| | | |
|---|---|---|
| 4,960,109 A | 10/1990 | Lele |
| 4,971,991 A | 11/1990 | Umemura et al. |
| 5,021,044 A | 6/1991 | Sharkawy et al. |
| 5,059,851 A | 10/1991 | Corl et al. |
| 5,069,664 A | 12/1991 | Guess et al. |
| 5,088,499 A | 2/1992 | Unger |
| 5,108,369 A | 4/1992 | Ganguly et al. |
| 5,129,883 A | 7/1992 | Black |
| 5,149,319 A | 9/1992 | Unger |
| 5,158,071 A | 10/1992 | Umemura et al. |
| 5,163,421 A | 11/1992 | Bernstein et al. |
| 5,178,620 A | 1/1993 | Eggers et al. |
| 5,185,071 A | 2/1993 | Serwer et al. |
| 5,197,946 A | 3/1993 | Tachibana |
| 5,226,421 A | 7/1993 | Frisbie et al. |
| 5,250,034 A | 10/1993 | Appling et al. |
| 5,261,291 A | 11/1993 | Schoch et al. |
| 5,267,954 A | 12/1993 | Nita |
| 5,267,985 A | 12/1993 | Shimada et al. |
| 5,269,291 A | 12/1993 | Carter |
| 5,271,406 A | 12/1993 | Ganguly et al. |
| 5,279,546 A | 1/1994 | Mische et al. |
| 5,282,785 A | 2/1994 | Shapland et al. |
| 5,286,254 A | 2/1994 | Shapland et al. |
| 5,295,484 A | 3/1994 | Marcus et al. |
| 5,304,115 A | 4/1994 | Pflueger et al. |
| 5,307,816 A | 5/1994 | Hashimoto et al. |
| 5,312,328 A | 5/1994 | Nita et al. |
| 5,313,949 A | 5/1994 | Yock |
| 5,315,998 A | 5/1994 | Tachibana et al. |
| 5,318,014 A | 6/1994 | Carter |
| 5,323,769 A | 6/1994 | Bommannan et al. |
| 5,327,891 A | 7/1994 | Rammler |
| 5,328,470 A | 7/1994 | Nabel et al. |
| 5,344,395 A | 9/1994 | Whalen et al. |
| 5,344,435 A | 9/1994 | Turner et al. |
| 5,345,940 A | 9/1994 | Seward et al. |
| 5,348,481 A | 9/1994 | Oritz |
| 5,351,693 A | 10/1994 | Taimisto et al. |
| 5,353,798 A | 10/1994 | Sieben |
| 5,354,279 A | 10/1994 | Hofling |
| 5,362,309 A | 11/1994 | Carter |
| 5,363,853 A | 11/1994 | Lieber |
| 5,368,036 A | 11/1994 | Tanaka et al. |
| 5,368,557 A | 11/1994 | Nita et al. |
| 5,368,558 A | 11/1994 | Nita |
| 5,370,675 A | 12/1994 | Edwards et al. |
| 5,372,138 A | 12/1994 | Crowley et al. |
| 5,380,273 A | 1/1995 | Dubrul et al. |
| 5,385,148 A | 1/1995 | Lesh et al. |
| 5,390,678 A | 2/1995 | Gesswein et al. |
| 5,397,293 A | 3/1995 | Alliger et al. |
| 5,399,158 A | 3/1995 | Lauer et al. |
| 5,401,237 A | 3/1995 | Tachibana et al. |
| 5,405,322 A | 4/1995 | Lennox et al. |
| 5,421,338 A | 6/1995 | Crowley et al. |
| 5,423,797 A | 6/1995 | Adrian et al. |
| 5,431,663 A | 7/1995 | Carter |
| 5,440,914 A | 8/1995 | Tachibana et al. |
| 5,445,155 A | 8/1995 | Sieben |
| 5,447,509 A | 9/1995 | Mills et al. |
| 5,447,510 A | 9/1995 | Jensen |
| 5,453,575 A | 9/1995 | O'Donnell et al. |
| 5,456,259 A | 10/1995 | Barlow et al. |
| 5,458,568 A | 10/1995 | Racchini et al. |
| 5,462,523 A | 10/1995 | Samson et al. |
| 5,465,726 A | 11/1995 | Dickinson et al. |
| 5,474,530 A | 12/1995 | Passafaro et al. |
| 5,474,531 A | 12/1995 | Carter |
| 5,498,238 A | 3/1996 | Shapland et al. |
| 5,509,896 A | 4/1996 | Carter |
| 5,514,092 A | 5/1996 | Forman et al. |
| 5,520,189 A | 5/1996 | Malinowski et al. |
| 5,523,058 A | 6/1996 | Umemura et al. |
| 5,533,986 A | 7/1996 | Mottola et al. |
| 5,542,917 A | 8/1996 | Nita et al. |
| 5,542,935 A | 8/1996 | Unger et al. |
| 5,558,092 A | 9/1996 | Unger et al. |
| 5,560,362 A | 10/1996 | Silwa, Jr. et al. |
| 5,569,197 A | 10/1996 | Helmus et al. |
| 5,582,586 A | 12/1996 | Tachibana et al. |
| 5,588,432 A | 12/1996 | Crowley |
| 5,603,327 A | 2/1997 | Eberle |
| 5,603,694 A | 2/1997 | Brown et al. |
| 5,606,974 A | 3/1997 | Castellano et al. |
| 5,617,851 A | 4/1997 | Lipkovker |
| 5,618,275 A | 4/1997 | Bock |
| 5,620,479 A | 4/1997 | Diederich |
| 5,624,382 A | 4/1997 | Oppelt |
| 5,628,728 A | 5/1997 | Tachibana et al. |
| 5,628,730 A | 5/1997 | Shapland et al. |
| 5,630,837 A | 5/1997 | Crowley |
| 5,648,098 A | 7/1997 | Porter |
| 5,656,016 A | 8/1997 | Ogden |
| 5,660,180 A | 8/1997 | Malinowski et al. |
| 5,660,909 A | 8/1997 | Tachibana et al. |
| 5,665,076 A | 9/1997 | Roth et al. |
| 5,695,460 A | 12/1997 | Siegel et al. |
| 5,697,897 A | 12/1997 | Buchholtz et al. |
| 5,713,831 A | 2/1998 | Olsson |
| 5,713,848 A | 2/1998 | Dubrul et al. |
| 5,720,710 A | 2/1998 | Tachibana et al. |
| 5,725,494 A | 3/1998 | Brisken |
| 5,728,062 A | 3/1998 | Brisken |
| 5,733,315 A | 3/1998 | Burdette et al. |
| 5,735,811 A | 4/1998 | Brisken |
| 5,772,632 A | 6/1998 | Forman |
| 5,775,338 A | 7/1998 | Hastings |
| 5,779,673 A | 7/1998 | Roth et al. |
| 5,807,395 A | 9/1998 | Mulier et al. |
| 5,817,021 A | 10/1998 | Reichenberger |
| 5,827,203 A | 10/1998 | Nita |
| 5,827,313 A | 10/1998 | Ream |
| 5,836,896 A | 11/1998 | Rosenschein |
| 5,836,940 A | 11/1998 | Gregory |
| 5,840,031 A | 11/1998 | Crowley |
| 5,846,218 A | 12/1998 | Brisken et al. |
| 5,876,345 A | 3/1999 | Eaton et al. |
| 5,916,192 A | 6/1999 | Nita et al. |
| 5,925,016 A | 7/1999 | Chornenky et al. |
| 5,928,186 A | 7/1999 | Homsma et al. |
| 5,931,805 A | 8/1999 | Brisken |
| 5,935,124 A | 8/1999 | Klumb et al. |
| 5,938,595 A | 8/1999 | Glass et al. |
| 5,941,868 A | 8/1999 | Kaplan et al. |
| 5,957,882 A | 9/1999 | Nita et al. |
| 5,957,941 A | 9/1999 | Ream |
| 5,971,949 A | 10/1999 | Levin et al. |
| 5,976,120 A | 11/1999 | Chow et al. |
| 5,984,882 A * | 11/1999 | Rosenschein et al. ............ 601/2 |
| 5,997,497 A | 12/1999 | Nita et al. |
| 6,001,069 A | 12/1999 | Tachibana et al. |
| 6,004,069 A | 12/1999 | Sudbury |
| 6,004,269 A | 12/1999 | Crowley et al. |
| 6,024,703 A | 2/2000 | Zanelli et al. |
| 6,024,718 A | 2/2000 | Chen et al. |
| 6,027,515 A | 2/2000 | Cimino |
| 6,033,397 A | 3/2000 | Laufer et al. |
| 6,053,868 A | 4/2000 | Geistert et al. |
| 6,059,731 A | 5/2000 | Seward et al. |
| 6,063,069 A | 5/2000 | Cragg et al. |
| 6,078,830 A | 6/2000 | Levin et al. |
| 6,088,613 A | 7/2000 | Unger |
| 6,089,573 A | 7/2000 | Udagawa |
| 6,096,000 A | 8/2000 | Tachibana et al. |
| 6,110,098 A | 8/2000 | Renirie et al. |
| 6,110,314 A | 8/2000 | Nix et al. |
| 6,113,546 A | 9/2000 | Suorsa et al. |
| 6,113,558 A | 9/2000 | Rosenschein et al. |
| 6,113,570 A | 9/2000 | Siegel et al. |
| 6,117,101 A | 9/2000 | Diederich et al. |
| 6,120,454 A | 9/2000 | Surosa et al. |
| 6,135,971 A | 10/2000 | Hutchinson et al. |
| 6,135,976 A | 10/2000 | Tachibana et al. |
| 6,149,599 A | 11/2000 | Schlesinger |
| 6,176,842 B1 | 1/2001 | Tachibana et al. |
| 6,196,973 B1 | 3/2001 | Lazenby et al. |

| | | |
|---|---|---|
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,231,516 B1 | 5/2001 | Keilman et al. |
| 6,235,024 B1 | 5/2001 | Tu |
| 6,238,347 B1 | 5/2001 | Nix et al. |
| 6,277,077 B1 | 8/2001 | Brisken et al. |
| 6,283,920 B1 | 9/2001 | Eberle et al. |
| 6,287,271 B1 | 9/2001 | Dubrul et al. |
| 6,296,610 B1 | 10/2001 | Schneider et al. |
| 6,296,619 B1 | 10/2001 | Brisken et al. |
| 6,299,597 B1 | 10/2001 | Buscemi et al. |
| 6,309,370 B1 | 10/2001 | Haim et al. |
| 6,312,402 B1 | 11/2001 | Hansmann et al. |
| 6,361,500 B1 | 3/2002 | Masters |
| 6,361,554 B1 | 3/2002 | Brisken |
| 6,366,719 B1 | 4/2002 | Heath et al. |
| 6,372,498 B2 | 4/2002 | Newman et al. |
| 6,379,320 B1 | 4/2002 | Lafon et al. |
| 6,387,052 B1 | 5/2002 | Jung, Jr. et al. |
| 6,391,042 B1 | 5/2002 | Cimino |
| 6,416,740 B1 | 7/2002 | Unger |
| 6,423,026 B1 | 7/2002 | Gesswein et al. |
| 6,433,464 B2 | 8/2002 | Jones |
| 6,437,487 B1 | 8/2002 | Mohr, III et al. |
| 6,456,863 B1 | 9/2002 | Levin et al. |
| 6,461,314 B1 | 10/2002 | Pant et al. |
| 6,464,680 B1 | 10/2002 | Brisken et al. |
| 6,503,202 B1 | 1/2003 | Hossack et al. |
| 6,506,584 B1 | 1/2003 | Chandler et al. |
| 6,508,775 B2 | 1/2003 | McKenzie et al. |
| 6,511,478 B1 | 1/2003 | Burnside et al. |
| 6,524,251 B2 | 2/2003 | Rabiner |
| 6,524,271 B2 | 2/2003 | Brisken et al. |
| 6,524,300 B2 | 2/2003 | Meglin |
| 6,537,224 B2 | 3/2003 | Mauchamp et al. |
| 6,537,306 B1 * | 3/2003 | Burdette et al. ............... 607/96 |
| 6,542,767 B1 | 4/2003 | McNichols et al. |
| 6,551,337 B1 | 4/2003 | Rabiner et al. |
| 6,560,837 B1 | 5/2003 | Hodjat et al. |
| 6,561,998 B1 | 5/2003 | Roth et al. |
| 6,562,021 B1 | 5/2003 | Derbin et al. |
| 6,575,922 B1 | 6/2003 | Fearnside et al. |
| 6,575,956 B1 | 6/2003 | Brisken et al. |
| 6,579,277 B1 | 6/2003 | Rabiner et al. |
| 6,579,279 B1 | 6/2003 | Rabiner et al. |
| 6,582,392 B1 | 6/2003 | Bennett et al. |
| 6,585,763 B1 | 7/2003 | Keilman et al. |
| 6,589,182 B1 | 7/2003 | Loftman et al. |
| 6,599,288 B2 | 7/2003 | Maguire et al. |
| 6,605,084 B2 | 8/2003 | Acker et al. |
| 6,607,502 B1 | 8/2003 | Maguire et al. |
| 6,635,017 B1 | 10/2003 | Moehring et al. |
| 6,647,755 B2 | 11/2003 | Rabiner et al. |
| 6,652,547 B2 | 11/2003 | Rabiner et al. |
| 6,660,013 B2 | 12/2003 | Rabiner et al. |
| 6,663,613 B1 | 12/2003 | Evans et al. |
| 6,676,626 B1 | 1/2004 | Bennett et al. |
| 6,695,781 B2 | 2/2004 | Rabiner et al. |
| 6,711,953 B2 | 3/2004 | Hayashi et al. |
| 6,723,063 B1 | 4/2004 | Zhang et al. |
| 6,726,698 B2 | 4/2004 | Cimino |
| 6,730,048 B1 | 5/2004 | Hare et al. |
| 6,733,451 B2 | 5/2004 | Rabiner et al. |
| 6,740,040 B1 | 5/2004 | Mandrusov et al. |
| 6,758,857 B2 | 7/2004 | Cioanta et al. |
| 6,824,515 B2 | 11/2004 | Suorsa et al. |
| 6,824,575 B1 | 11/2004 | Otomo et al. |
| 6,855,123 B2 | 2/2005 | Nita |
| 6,921,371 B2 | 7/2005 | Wilson |
| 6,929,633 B2 | 8/2005 | Evans et al. |
| 6,942,620 B2 | 9/2005 | Nita et al. |
| 6,958,040 B2 | 10/2005 | Oliver et al. |
| 6,979,293 B2 | 12/2005 | Hansmann |
| 7,077,820 B1 | 7/2006 | Kadziauskas et al. |
| 7,089,063 B2 | 8/2006 | Lesh et al. |
| 7,141,044 B2 | 11/2006 | Gentsler |
| 7,220,239 B2 | 5/2007 | Wilson et al. |
| 7,341,569 B2 | 3/2008 | Soltani et al. |
| 7,771,372 B2 | 8/2010 | Wilson |
| 2001/0000791 A1 | 5/2001 | Suorsa et al. |
| 2001/0007861 A1 | 7/2001 | Newman et al. |
| 2001/0007940 A1 | 7/2001 | Tu et al. |
| 2001/0025190 A1 | 9/2001 | Weber et al. |
| 2001/0037106 A1 | 11/2001 | Shadduck et al. |
| 2001/0039419 A1 | 11/2001 | Francischelli et al. |
| 2001/0041842 A1 | 11/2001 | Eberie et al. |
| 2001/0041880 A1 | 11/2001 | Brisken et al. |
| 2002/0000763 A1 | 1/2002 | Jones |
| 2002/0019644 A1 | 2/2002 | Hastings et al. |
| 2002/0032394 A1 | 3/2002 | Brisken et al. |
| 2002/0045890 A1 | 4/2002 | Celliers et al. |
| 2002/0068869 A1 | 6/2002 | Brisken et al. |
| 2002/0077550 A1 | 6/2002 | Rabiner et al. |
| 2002/0087083 A1 | 7/2002 | Nix et al. |
| 2002/0099292 A1 | 7/2002 | Brisken et al. |
| 2002/0133111 A1 | 9/2002 | Shadduk |
| 2002/0188276 A1 | 12/2002 | Evans et al. |
| 2003/0036705 A1 | 2/2003 | Hare et al. |
| 2003/0040501 A1 | 2/2003 | Newman et al. |
| 2003/0069525 A1 | 4/2003 | Brisken et al. |
| 2003/0109812 A1 | 6/2003 | Corl et al. |
| 2003/0135262 A1 | 7/2003 | Dretler et al. |
| 2003/0220568 A1 | 11/2003 | Hansmann et al. |
| 2004/0001809 A1 | 1/2004 | Brisken et al. |
| 2004/0019318 A1 | 1/2004 | Wilson et al. |
| 2004/0024347 A1 | 2/2004 | Wilson et al. |
| 2004/0024393 A1 | 2/2004 | Nita et al. |
| 2004/0039311 A1 | 2/2004 | Nita et al. |
| 2004/0049148 A1 | 3/2004 | Rodriguez et al. |
| 2004/0068189 A1 | 4/2004 | Wilson et al. |
| 2004/0138570 A1 | 7/2004 | Nita et al. |
| 2004/0162571 A1 | 8/2004 | Rabiner et al. |
| 2004/0243062 A1 | 12/2004 | Henry |
| 2005/0043629 A1 | 2/2005 | Rabiner et al. |
| 2005/0043753 A1 | 2/2005 | Rabiner et al. |
| 2005/0096669 A1 | 5/2005 | Rabiner et al. |
| 2005/0113688 A1 | 5/2005 | Nita et al. |
| 2005/0119679 A1 | 6/2005 | Rabiner et al. |
| 2005/0124877 A1 | 6/2005 | Nita et al. |
| 2005/0137520 A1 | 6/2005 | Rule et al. |
| 2005/0187513 A1 | 8/2005 | Rabiner et al. |
| 2005/0187514 A1 | 8/2005 | Rabiner et al. |
| 2005/0192556 A1 | 9/2005 | Soltani et al. |
| 2005/0197619 A1 | 9/2005 | Rule et al. |
| 2005/0209578 A1 | 9/2005 | Evans et al. |
| 2005/0215942 A1 | 9/2005 | Abrahamson et al. |
| 2005/0215946 A1 | 9/2005 | Hansmann et al. |
| 2005/0288695 A1 | 12/2005 | Jenson et al. |
| 2006/0116610 A1 | 6/2006 | Hare |
| 2006/0173387 A1 | 8/2006 | Hansmann et al. |
| 2007/0265560 A1 | 11/2007 | Soltani et al. |

FOREIGN PATENT DOCUMENTS

| | | |
|---|---|---|
| EP | 0 529 675 | 8/1992 |
| EP | 0 629 382 | 12/1994 |
| EP | 0744189 | 11/1996 |
| EP | 0 746 245 | 12/1996 |
| EP | 1 090 658 | 4/2001 |
| JP | 52115591 | 9/1977 |
| JP | 2180275 | 7/1990 |
| WO | WO 89/04142 | 5/1989 |
| WO | WO 92/00113 | 1/1992 |
| WO | WO 95/01751 | 1/1995 |
| WO | WO 95/05866 | 3/1995 |
| WO | WO 95/26777 | 12/1995 |
| WO | WO 96/04955 | 2/1996 |
| WO | WO 96/27341 | 9/1996 |
| WO | WO 96/29935 | 10/1996 |
| WO | WO 96/36286 | 11/1996 |
| WO | WO 97/19645 | 5/1997 |
| WO | WO 98/11826 | 3/1998 |
| WO | WO 98/18391 | 5/1998 |
| WO | WO 98/48711 | 11/1998 |
| WO | WO 98/56462 | 12/1998 |
| WO | WO 99/32184 | 7/1999 |

| | | |
|---|---|---|
| WO | WO 99/33500 | 7/1999 |
| WO | WO 99/34858 | 7/1999 |
| WO | WO 99/39647 | 8/1999 |
| WO | WO 99/44512 | 9/1999 |
| WO | WO 00/00095 A | 1/2000 |
| WO | WO 00/38580 | 7/2000 |
| WO | WO 00/69341 | 11/2000 |
| WO | WO 01/54754 | 8/2001 |
| WO | WO 01/87174 A1 | 11/2001 |
| WO | WO 01/95788 | 12/2001 |
| WO | WO 02/13678 A2 | 2/2002 |
| WO | WO 02/15803 | 2/2002 |
| WO | WO 02/15804 | 2/2002 |
| WO | WO 03/051208 A1 | 6/2003 |
| WO | WO 2005/027756 | 3/2005 |
| WO | WO 2005/084552 | 9/2005 |
| WO | WO 2005/084553 | 9/2005 |

OTHER PUBLICATIONS

Hynynen et al.; "Small Cylindrical Ultrasound Sources for Induction of Hyperthermia via Body Cavities or Interstitial Implants"; Arizona Cancer Center and Department of Radiation Oncology, University of Arizona Health Sciences Center; vol. 9, No. 2; pp. 263-274; 1993.

Lee et al.; "Arrays of Multielement Ultrasound Applicators for Interstitial Hyperthermia"; IEEE Transactions on Biomedical Engineering; vol. 46, No. 7; Jul. 1999.

Schafer et al., "Influence of Ultrasound Operating Parameters on Ultrasound Induced Thromolysis in Vitro"; Ultrasound in Med. & Biol., vol. 23, No. 6, pp. 841-847.

Tsetis et al., "Potential Benefits From Heating the High-Dose Rtpa Boluses Used in Catheter-Directed Thrombolysis for Acute/Subacute Lower Limb Ischemia", J Endovasc. Ther. 10:739-744 (2003).

* cited by examiner

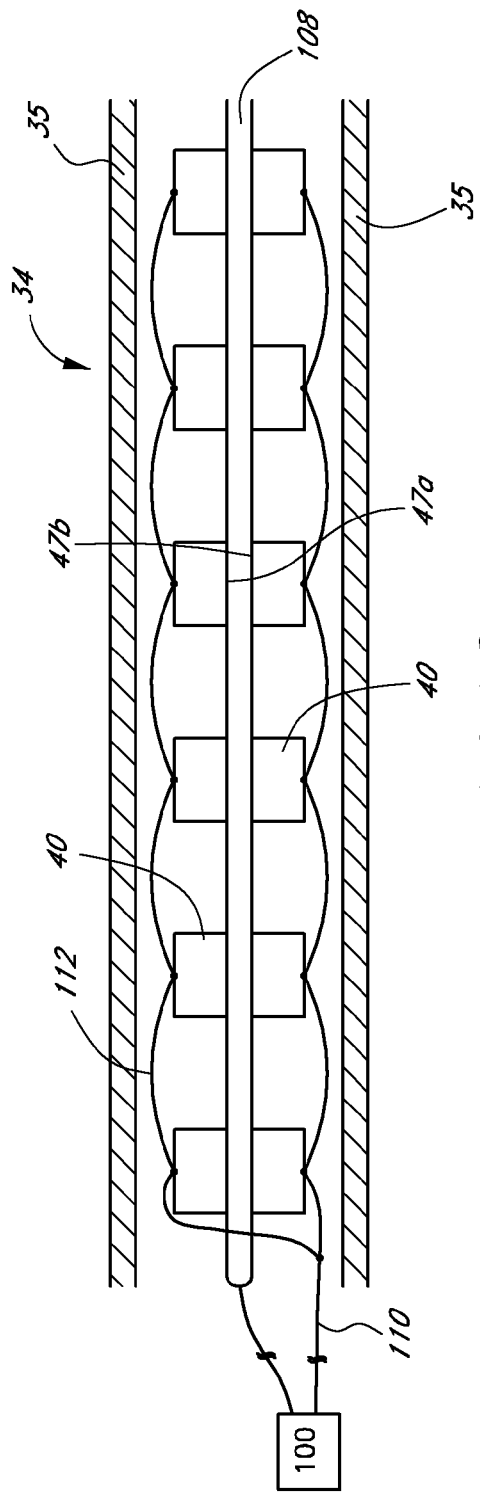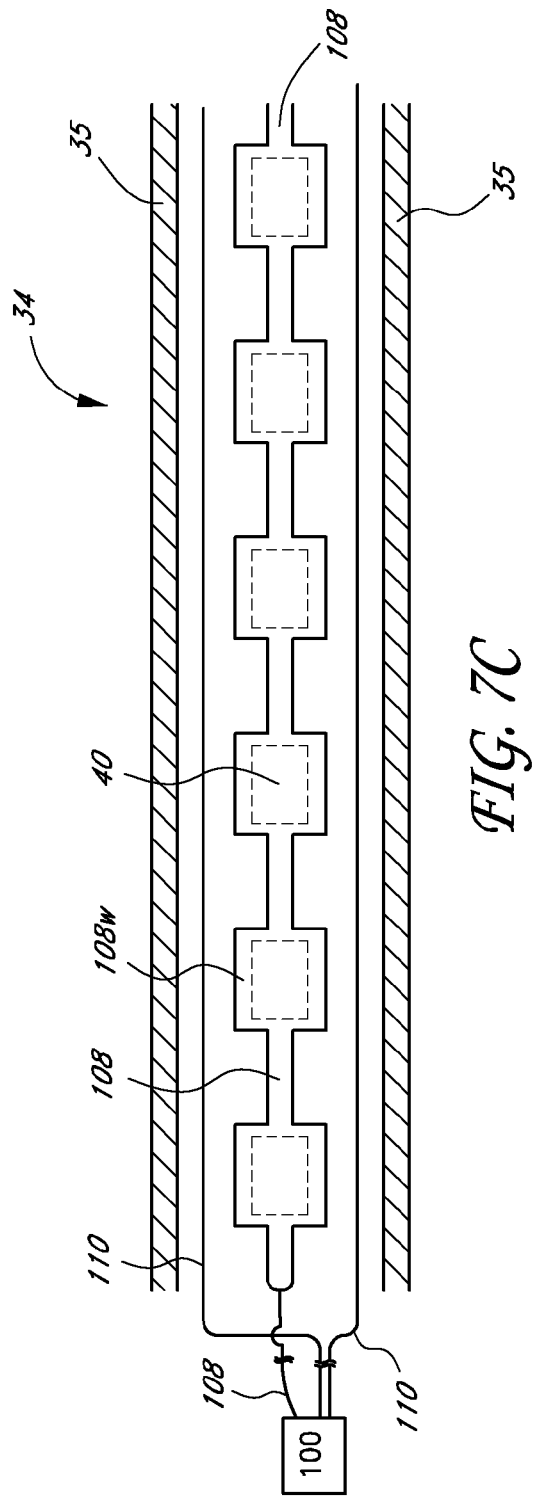

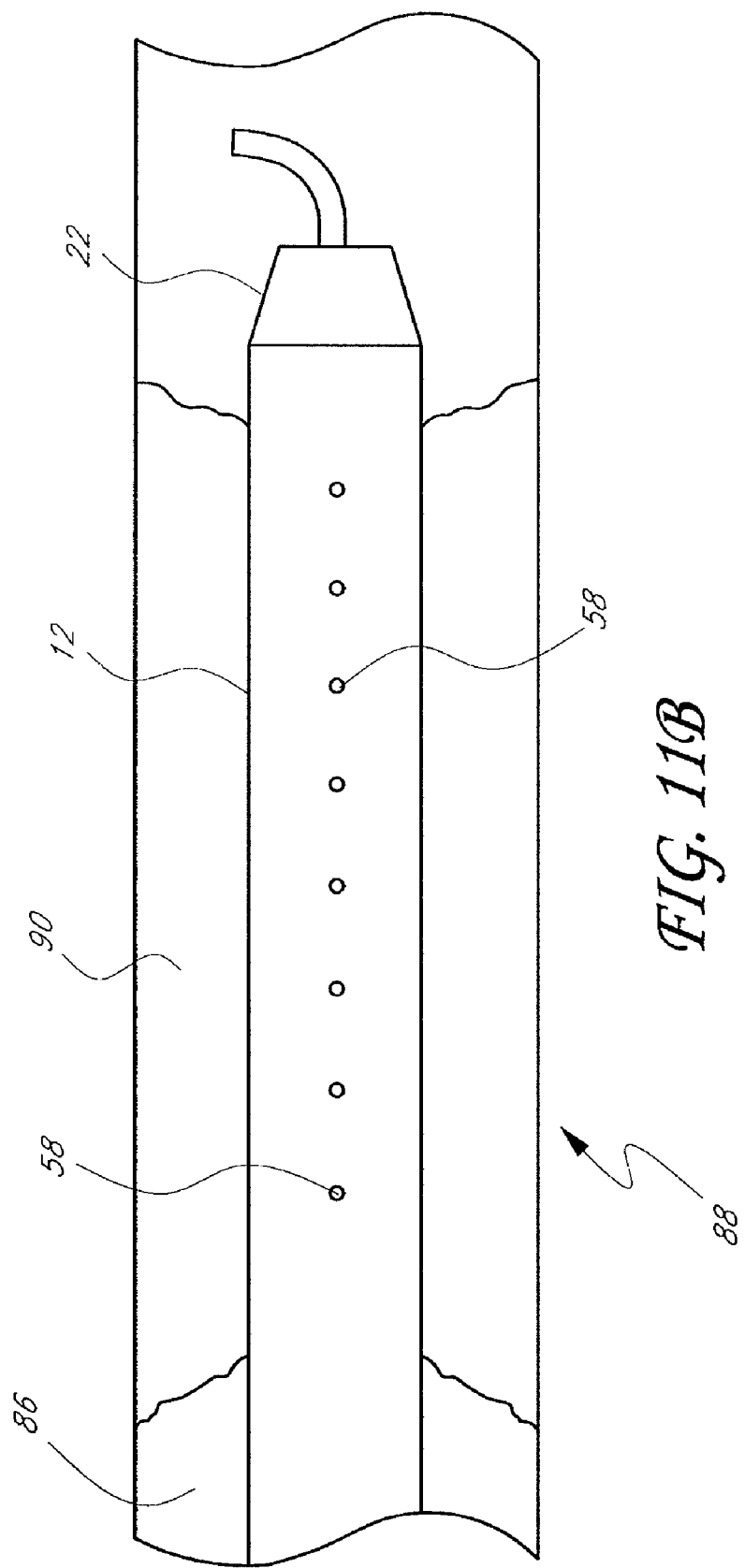

CATHETER WITH MULTIPLE ULTRASOUND RADIATING MEMBERS

CROSS-REFERENCE TO RELATED APPLICATIONS

This application claims the priority benefit to U.S. Provisional No. 60/855,172 filed Oct. 27, 2006, the entirety of which is hereby incorporated by reference herein.

BACKGROUND OF THE INVENTION

1. Field of the Invention

The present invention relates generally to an ultrasonic catheter and more specifically to an ultrasonic catheter configured to deliver ultrasonic energy and a therapeutic compound to a treatment site.

2. Description of the Related Art

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site in a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, such ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing dissolution compounds directly to the occlusion site. Ultrasonic energy generated by the ultrasound assembly enhances the therapeutic effect of the dissolution compounds. For example, in one application of such an ultrasonic catheter, an ultrasound-enhanced thrombolytic therapy dissolves blood clots in arteries and veins in the treatment of diseases such as peripheral arterial occlusion or deep vein thrombosis. In such applications, ultrasonic energy enhances thrombolysis with agents such as urokinase, tissue plasminogen activator ("TPA") and the like.

Ultrasonic catheters can also be used to enhance gene therapy at a treatment site within the patient's body. For example, U.S. Pat. No. 6,135,976 discloses an ultrasonic catheter having one or more expandable sections capable of occluding a section of a body lumen, such as a blood vessel. A gene therapy composition is then delivered to the occluded vessel through the catheter fluid delivery lumen. Ultrasonic energy generated by the ultrasound assembly is applied to the occluded vessel, thereby enhancing the delivery of a genetic composition into the cells of the occluded vessel.

Ultrasonic catheters can also be used to enhance delivery and activation of light activated drugs. For example, U.S. Pat. No. 6,176,842 discloses methods for using an ultrasonic catheter to treat biological tissues by delivering a light activated drug to the biological tissues and exposing the light activated drug to ultrasound energy.

SUMMARY OF THE INVENTION

In certain medical procedures, it is desirable to provide ultrasonic energy along a substantial length of a body lumen. For example, long segment peripheral arterial occlusions, such as those in the arteries of the leg, may have an axial length in the range of 10 to 50 cm. To date, it has been difficult to design an ultrasonic catheter capable of efficiently applying ultrasound energy over such lengths.

One solution is disclosed in U.S. Pat. No. 6,296,610. This patent discloses a catheter with a plurality of transducers that are moved back and forth within the catheter through the treatment zone. However, this arrangement is generally undesirable because it requires a translation system for moving the ultrasonic elements within the catheter.

Another solution for emitting ultrasonic energy over such lengths is to provide the ultrasonic catheter with a plurality of ultrasonic transducers spaced along a distal region of the catheter. Such an arrangement faces several technical hurdles. For example, because the ultrasonic transducers are relatively rigid, the catheter may become too inflexible to be navigated through the lumens of the patient's body. One solution is to use smaller transducers as disclosed in U.S. Patent Publication No. 2004/0024347, published Feb. 5, 2004, the entirety of which is incorporated by reference herein. In this publication, a catheter is disclosed which can utilize sixty ultrasound radiating members 40 arranged in pairs. The 30 pairs of ultrasound radiating members can be spaced over a length of approximately 30 to 50 cm and arranged in groups. However, within these broad ranges there is a need to select the number and spacing which balances the need to provide enhanced bioefficacy while reducing or minimizing the number of ultrasound radiating members. In general, it would be desirable to reduce or minimize the number or ultrasound radiating members while substantially maintaining bioefficacy so as to reduce the parts and cost of the catheter and improve the overall flexibility of the catheter.

A need, therefore, exists for an improved ultrasonic catheter capable of providing ultrasonic energy over a substantial length of a body lumen.

Accordingly, one embodiment of the present invention comprises a catheter system for delivering ultrasonic energy to a treatment site. The catheter system comprises a tubular body having a proximal end, a distal end and a treatment zone located between the distal end and the proximal end. The catheter system further comprises an ultrasonic assembly positioned within the treatment zone. The ultrasonic assembly comprises a plurality of ultrasound elements, each ultrasound element having a longitudinal length and a longitudinal spacing between longitudinal centers of longitudinally adjacent ultrasound elements. The catheter is configured such that the average power supplied to the ultrasound elements in the treatment zone has a longitudinal density between 0.2 and about 1.0 W/cm.

In some embodiments, the catheter system further comprises a therapeutic compound delivery lumen that extends through the tubular body and terminates in at least one outlet positioned in the treatment zone.

In some embodiments of the catheter system, the ultrasonic assembly is positioned within an inner core.

In some embodiments of the catheter system, the inner core can be removably inserted into the tubular body so as to position the ultrasonic assembly in the treatment zone.

In some embodiments of the catheter system, the ultrasound elements are electrically coupled to a first wire and a second wire.

In some embodiments of the catheter system further comprises a control system configured such that a voltage can be applied simultaneously across the first and second wires to drive the ultrasound elements.

In some embodiments of the catheter system, the treatment zone has a greater acoustic transparency than a proximal region of the tubular body.

In some embodiments of the catheter system, each ultrasound element comprises a plurality of ultrasound transducer pairs. Each ultrasound transducer pair comprises a first transducer with a first face and a second transducer with a second face, the first face of the first transducer and the second face of the second transducer facing each other.

In some embodiments of the catheter system, the longitudinal density is between about 0.3 and about 0.6 W/cm.

In some embodiments of the catheter system, the longitudinal density is between about 0.4 and about 0.5 W/cm.

Another embodiment of the present invention comprises a catheter system for delivering ultrasonic energy and a therapeutic compound to a treatment site within a body lumen. The catheter system comprises a tubular body having a proximal end, a distal end and an energy delivery section positioned between the proximal end and the distal end. The catheter system further comprises a fluid delivery lumen extending at least partially through the tubular body and having at least one outlet in the energy delivery section. The catheter system further comprises an inner core configured for insertion into the tubular body. The inner core comprises a plurality of ultrasound radiating elements each ultrasound element having a longitudinal length and a longitudinal spacing between longitudinal centers of longitudinally adjacent ultrasound elements. The inner core is configured to be positioned within the energy delivery section. The energy delivery section has a length greater than about 10 cm and the plurality of ultrasound elements that are positioned within the energy delivery section and the catheter system supplies an average power to the ultrasound elements such that the energy delivery section has longitudinal power density between about 0.3 and about 0.6 W/cm.

In some embodiments of the catheter system, the fluid delivery lumen comprises a plurality of lumens formed within the tubular body.

In some embodiments of the catheter system, the plurality of ultrasound radiating elements are electrically coupled into a plurality of electrical groups, each group of ultrasound radiating members independently drivable by a control system.

In some embodiments of the catheter system, the ultrasound radiating members are allocated into at least five electrical groups.

In some embodiments of the catheter system, the ultrasonic radiating elements comprise ultrasonic transducers in the shape of a rectangular bar.

In some embodiments of the catheter system, the longitudinal spacing between ultrasound elements is about 1.0 cm.

Another embodiment of the present invention comprises a catheter system for delivering ultrasonic energy to a treatment site. The catheter system comprises a tubular body having a proximal end, a distal end and a treatment zone located between the distal end and the proximal end. The catheter system further comprises an ultrasonic assembly positioned within the treatment zone and means for providing an average longitudinal power density between about 0.2 and about 1.0 W/cm within the treatment zone.

In some embodiments of the catheter system, the longitudinal density is between about 0.3 and about 0.6 W/cm.

In some embodiments of the catheter system, the longitudinal density is between about 0.4 and about 0.5 W lcm.

In some embodiments of the catheter system, the longitudinal density is about 0.45 W/cm.

BRIEF DESCRIPTION OF THE DRAWINGS

FIG. 7B is a cross-sectional view of the ultrasound assembly of FIG. 7A taken along line 7B-7B.

FIG. 7C is a cross-sectional view of the ultrasound assembly of FIG. 7A taken along line 7C-7C.

FIG. 11B is a side view of the distal end of an ultrasonic catheter positioned at the treatment site of FIG. 11A.

DETAILED DESCRIPTION OF THE PREFERRED EMBODIMENT

Figure 1:
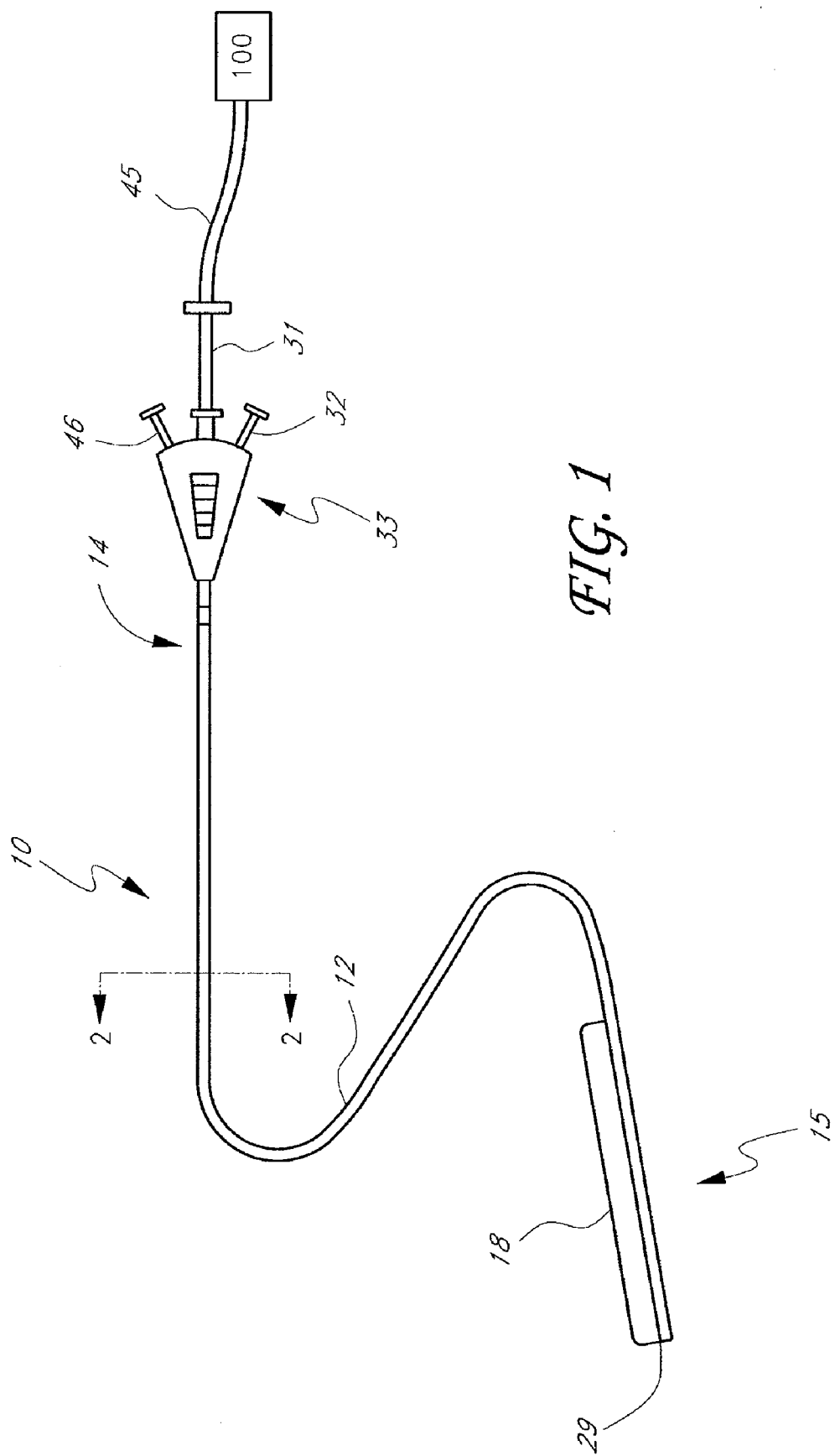
FIG. 1 is a schematic illustration of an ultrasonic catheter configured for insertion into large vessels of the human body.

As described above, it is desired to provide an ultrasonic catheter having various features and advantages. Examples of such features and advantages include the ability to apply ultrasonic energy to a treatment site. In another embodiment, the catheter has the ability to deliver a therapeutic compound to the treatment site. Preferred embodiments of an ultrasonic catheter having certain of these features and advantages are described herein. Methods of using such an ultrasonic catheter are also described herein.

The ultrasonic catheters described herein can be used to enhance the therapeutic effects of therapeutic compounds at a treatment site within a patient's body. As used herein, the term "therapeutic compound" refers broadly, without limitation, to a drug, medicament, dissolution compound, genetic material or any other substance capable of effecting physiological functions. Additionally, any mixture comprising any such substances is encompassed within this definition of "therapeutic compound", as well as any substance falling within the ordinary meaning of these terms. The enhancement of the effects of therapeutic compounds using ultrasonic energy is described in U.S. Pat. Nos. 5,318,014, 5,362,309, 5,474,531, 5,628,728, 6,001,069 and 6,210,356, the entire disclosure of which are hereby incorporated herein by reference. Specifically, for applications that treat human blood vessels that have become partially or completely occluded by plaque, thrombi, emboli or other substances that reduce the blood carrying capacity of a vessel, suitable therapeutic compounds include, but are not limited to, an aqueous solution containing Heparin, Uronkinase, Streptokinase, TPA and BB-10153 (manufactured by British Biotech, Oxford, UK).

Certain features and aspects of the ultrasonic catheters disclosed herein may also find utility in applications where the ultrasonic energy itself provides a therapeutic effect. Examples of such therapeutic effects include preventing or reducing stenosis and/or restenosis; tissue ablation, abrasion or disruption; promoting temporary or permanent physiological changes in intracellular or intercellular structures; and rupturing micro-balloons or micro-bubbles for therapeutic compound delivery. Further information about such methods can be found in U.S. Pat. Nos. 5,261,291 and 5,431,663, the entire disclosure of which are hereby incorporated herein by reference.

The ultrasonic catheters described herein are configured for applying ultrasonic energy over a substantial length of a body lumen, such as, for example, the larger vessels located in the leg. However, it should be appreciated that certain features and aspects of the present invention may be applied to catheters configured to be inserted into the small cerebral vessels, in solid tissues, in duct systems and in body cavities. Additional embodiments that may be combined with certain features and aspects of the embodiments described herein are described in U.S. Publication No. 2004/0019318 entitled "Ultrasound Assembly For Use With A Catheter" and filed Nov. 7, 2002, the entire disclosure of which is hereby incorporated herein by reference.

With initial reference to FIG. 1, FIG. 1 schematically illustrates an ultrasonic catheter 10 configured for use in the large vessels of a patient's anatomy. For example, the ultrasonic catheter 10 illustrated in FIG. 1 can be used to treat long segment peripheral arterial occlusions, such as those in the vascular system of the leg.

As illustrated in FIG. 1, the ultrasonic catheter 10 generally comprises a multi-component, elongate flexible tubular body 12 having a proximal region 14 and a distal region 15. The tubular body 12 includes a flexible energy delivery section 18 located in the distal region 15 of the catheter 10. The tubular body 12 and other components of the catheter 10 can be manufactured in accordance with any of a variety of techniques well known in the catheter manufacturing field. Suitable materials and dimensions can be readily selected based on the natural and anatomical dimensions of the treatment site and on the desired percutaneous access site.

For example, in a preferred embodiment the proximal region 14 of the tubular body 12 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the tubular body 12 is reinforced by braiding, mesh or other constructions to provide increased kink resistance and pushability. For example, nickel titanium or stainless steel wires can be placed along or incorporated into the tubular body 12 to reduce kinking.

In an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths may by appropriate for other applications.

The energy delivery section 18 of the tubular body 12 preferably comprises a material that is thinner than the material comprising the proximal region 14 of the tubular body 12 or a material that has a greater acoustic transparency. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 may be formed from the same material or a material of the same thickness as the proximal region 14.

In certain embodiments, the tubular body 12 is divided into at least three sections of varying stiffness. The first section, which preferably includes the proximal region 14, has a relatively higher stiffness. The second section, which is located in an intermediate region between the proximal region 14 and the distal region 15 of the tubular body 12, has a relatively lower stiffness. This configuration further facilitates movement and placement of the catheter 10. The third section, which preferably includes the energy delivery section 18, is generally lower stiffness than the second section in spite of the presence of the ultrasound radiating members 40.

Figure 2:
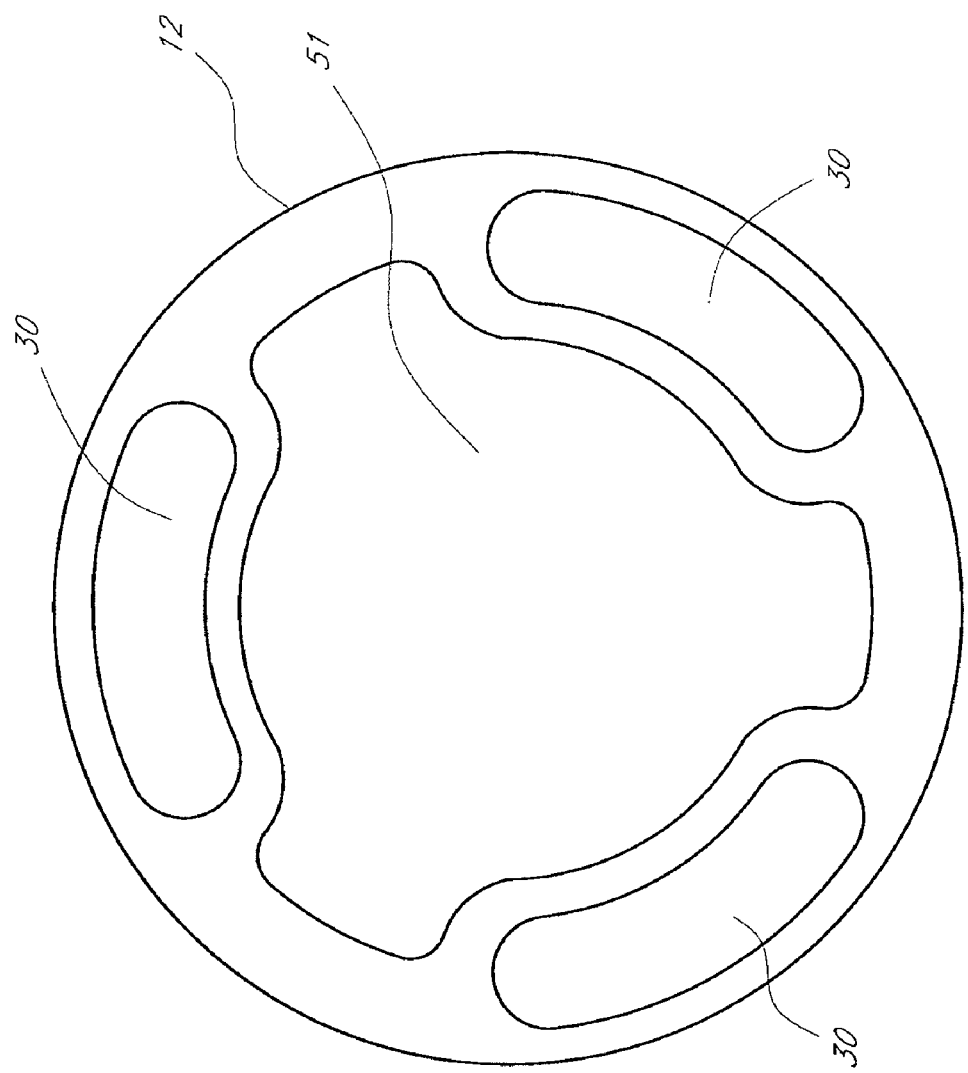
FIG. 2 is a cross-sectional view of the ultrasonic catheter of FIG. 1 taken along line 2-2.

FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. The arrangement of the fluid delivery lumens 30 preferably provides a hollow central lumen 51 passing through the tubular body 12. The cross-section of the tubular body 12, as illustrated in FIG. 2, is preferably substantially constant along the length of the catheter 10. Thus, in such embodiments, substantially the same cross-section is present in both the proximal region 14 and the distal region 15 of the catheter 10, including the energy delivery section 18.

In certain embodiments, the central lumen 51 has a minimum diameter greater than about 0.030 inches. In another embodiment, the central lumen 51 has a minimum diameter greater than about 0.037 inches. In one preferred embodiment, the fluid delivery lumens 30 have dimensions of about 0.026 inches wide by about 0.0075 inches high, although other dimensions may be used in other applications.

As described above, the central lumen 51 preferably extends through the length of the tubular body 12. As illustrated in FIG. 1, the central lumen 51 preferably has a distal exit port 29 and a proximal access port 31. The proximal access port 31 forms part of the backend hub 33, which is attached to the proximal region 14 of the catheter 10. The backend hub preferably further comprises cooling fluid fitting 46, which is hydraulically connected to the central lumen 51. The backend hub 33 also preferably comprises a therapeutic compound inlet port 32, which is in hydraulic connection with the fluid delivery lumens 30, and which can be hydraulically coupled to a source of therapeutic compound via a hub such as a Luer fitting.

Figure 3:
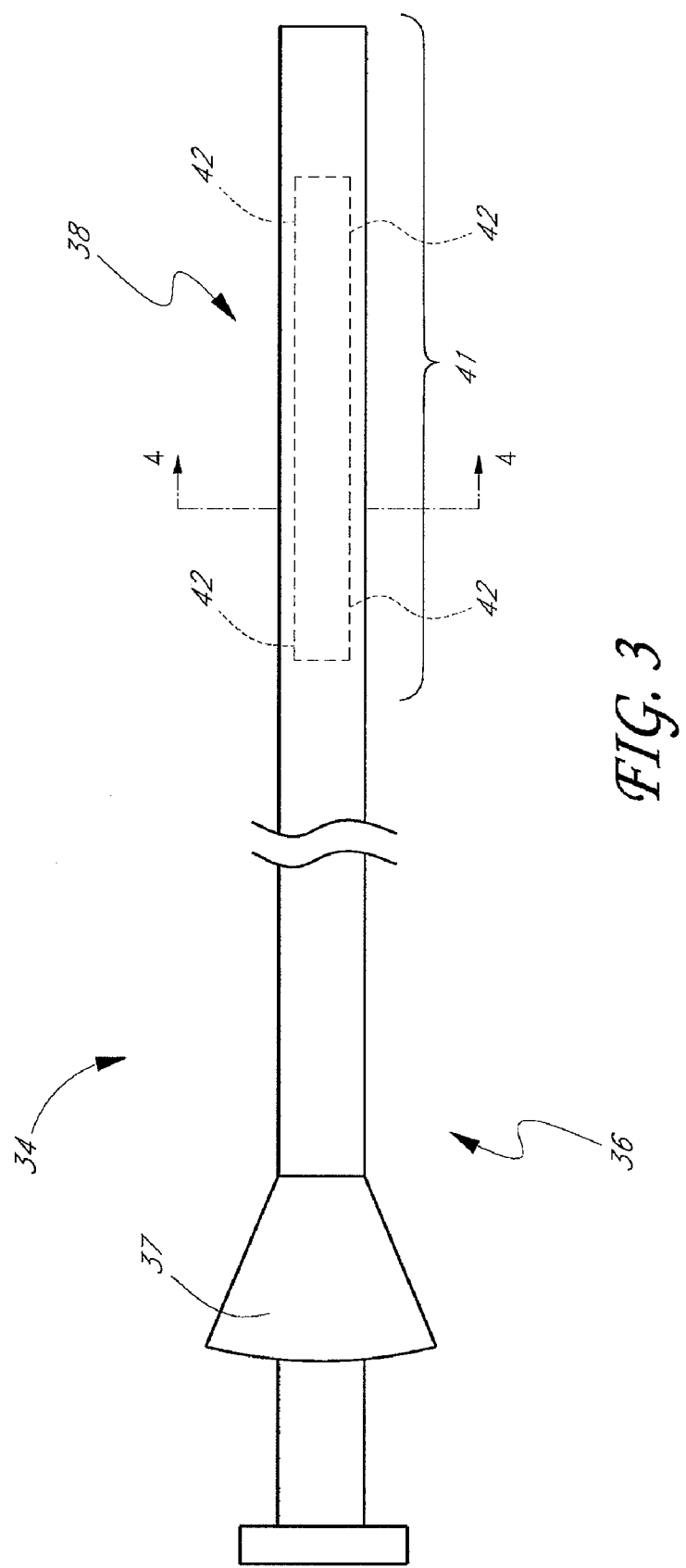
FIG. 3 is a schematic illustration of an elongate inner core configured to be positioned within the central lumen of the catheter illustrated in FIG. 2.

The central lumen 51 is configured to receive an elongate inner core 34 of which a preferred embodiment is illustrated in FIG. 3. The elongate inner core 34 preferably comprises a proximal region 36 and a distal region 38. Proximal hub 37 is fitted on the inner core 34 at one end of the proximal region 36. One or more ultrasound radiating members are positioned within an inner core energy delivery section 41 located within the distal region 38. The ultrasound radiating members 40 form an ultrasound assembly 42, which will be described in detail below.

Figure 4:
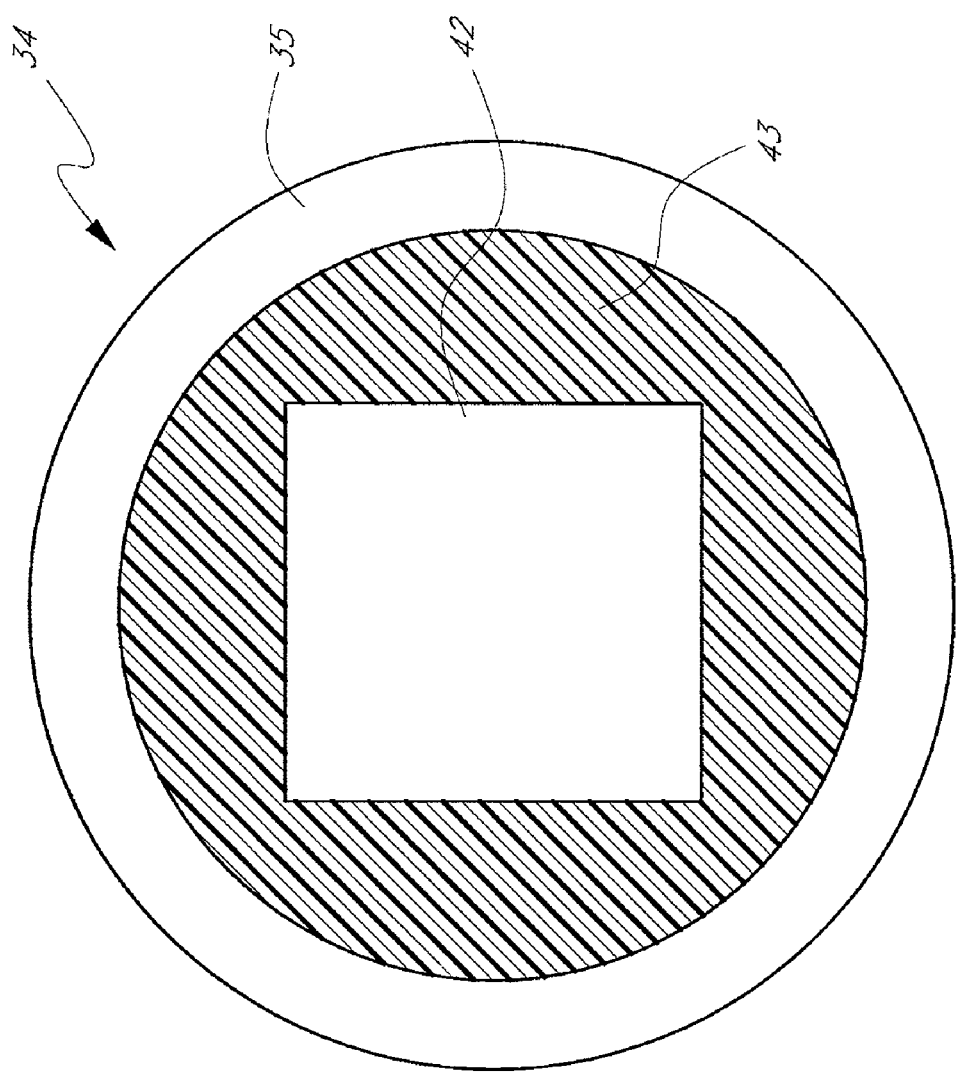
FIG. 4 is a cross-sectional view of the elongate inner core of FIG. 3 taken along line 4-4.

As shown in the cross-section illustrated in FIG. 4, which is taken along lines 4-4 in FIG. 3, the inner core 34 preferably has a cylindrical shape, with an outer diameter that permits the inner core 34 to be inserted into the central lumen 51 of the tubular body 12 via the proximal access port 31. Suitable outer diameters of the inner core 34 include, but are not limited to, about 0.010 inches to about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 preferably comprises a cylindrical outer body 35 that houses the ultrasound assembly 42. The ultrasound assembly 42 comprises wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to a control system 100 via cable 45 (illustrated in FIG. 1). Preferably, an electrically insulating potting material 43 fills the inner core 34, surrounding the ultrasound assembly 42, thus preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
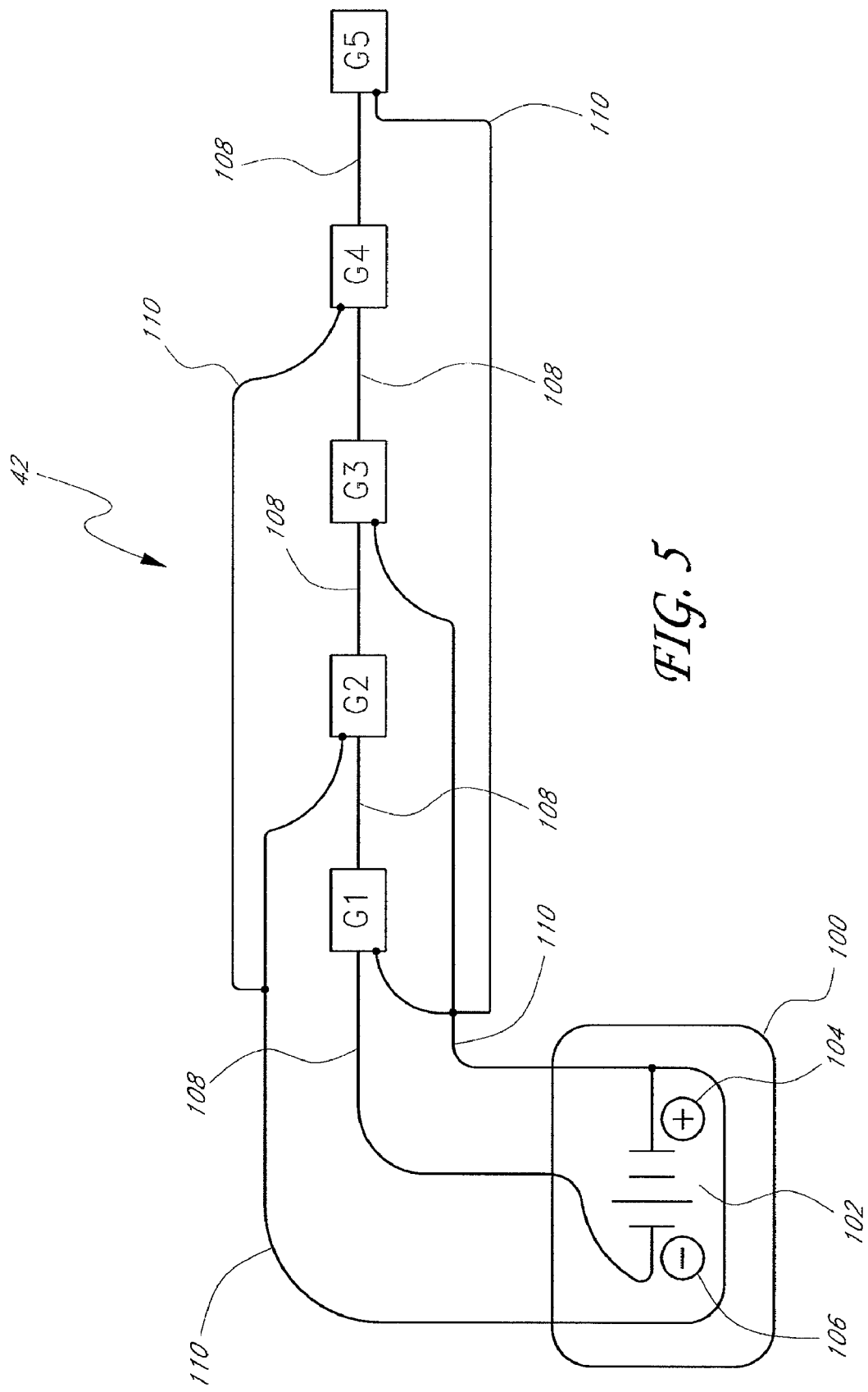
FIG. 5 is a schematic wiring diagram illustrating a preferred technique for electrically connecting five groups of ultrasound radiating members to form an ultrasound assembly.
Figure 6:
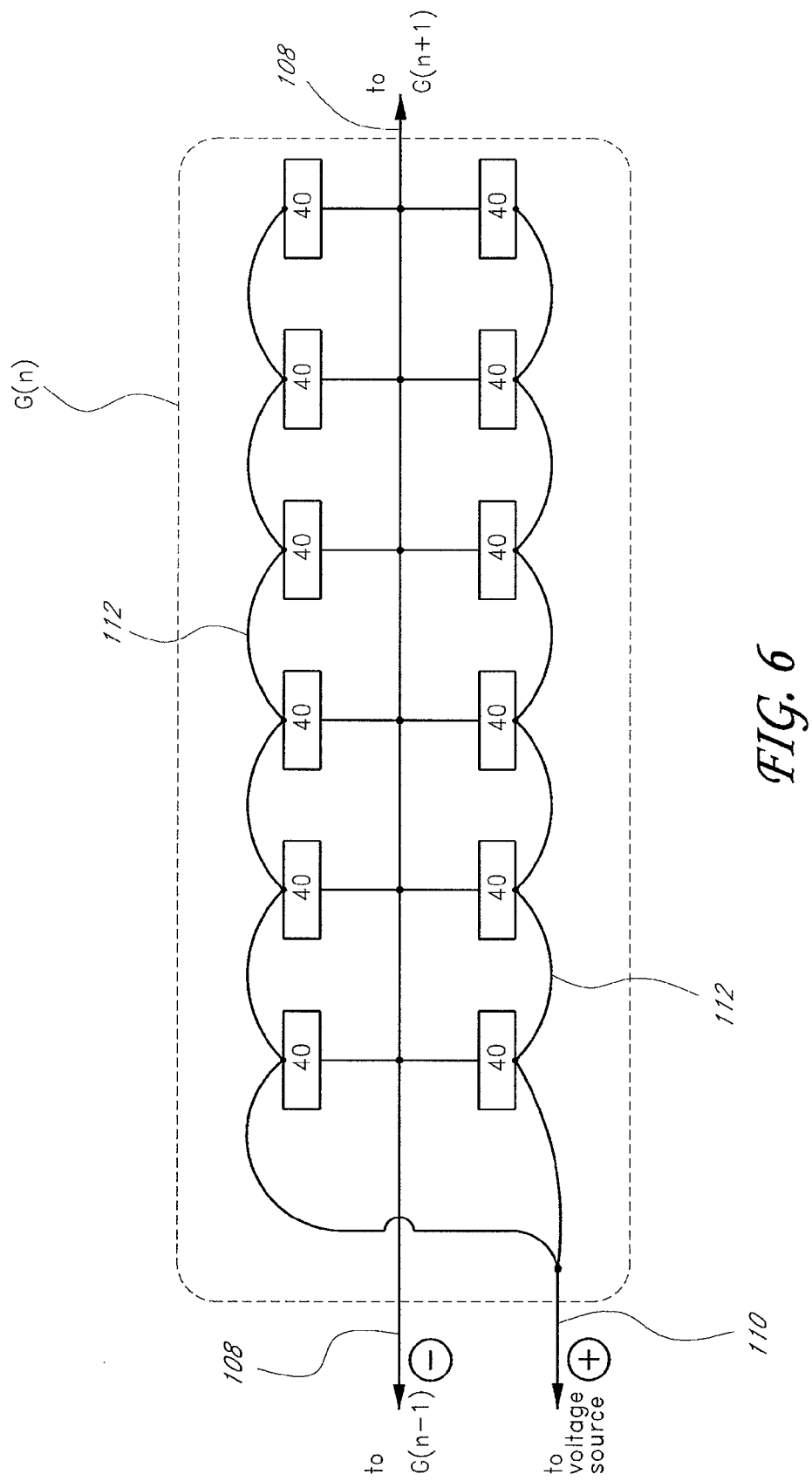
FIG. 6 is a schematic wiring diagram illustrating a preferred technique for electrically connecting one of the groups of FIG. 5.

In a preferred embodiment, the ultrasound assembly 42 comprises a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control system 100.

As used herein, the terms "ultrasonic energy", "ultrasound" and "ultrasonic" are broad terms, having their ordinary meanings, and further refer to, without limitation, mechanical energy transferred through longitudinal pressure or compression waves. Ultrasonic energy can be emitted as continuous or pulsed waves, depending on the requirements of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy has a frequency between about 20 kHz and about 20 MHz. For example, in one embodiment, the waves have a frequency between about 500 kHz and about 20 MHz. In another embodiment, the waves have a frequency between about 1 MHz and about 3 MHz. In yet another embodiment, the waves have a frequency of about 2 MHz. The average acoustic power is between about 0.01 watts and 300 watts. In one embodiment, the average acoustic power is about 15 watts.

As used herein, the term "ultrasound radiating member or element" refers to any apparatus capable of producing ultrasonic energy. For example, in one embodiment, an ultrasound radiating member comprises an ultrasonic transducer, which converts electrical energy into ultrasonic energy. A suitable example of an ultrasonic transducer for generating ultrasonic energy from electrical energy includes, but is not limited to, piezoelectric ceramic oscillators. Piezoelectric ceramics typically comprise a crystalline material, such as quartz, that change shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

Still referring to FIG. 5, the control circuitry 100 preferably comprises, among other things, a voltage source 102. The voltage source 102 comprises a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 6, is connected to the positive terminal 104 via one of the lead wires 110, and to the negative terminal 106 via the common wire 108.

Referring now to FIG. 6, each group G1-G5 can comprise a plurality of ultrasound radiating members 40. Each of the ultrasound radiating members 40 is electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5. It should also be appreciated that, as described below, the ultrasound elements are arranged in pairs which are generally located at the same longitudinal position on the catheter. Such pairs of ultrasound radiating members 40 will often be referred to herein as ultrasound radiating elements. Thus, in the illustrated embodiment each group comprises 6 ultrasound elements with each ultrasound element comprising a pair of ultrasound radiating members 40. In modified embodiments, the ultrasound radiating element can comprise more or less than two ultrasound radiating members. 40.

Figure 7A:
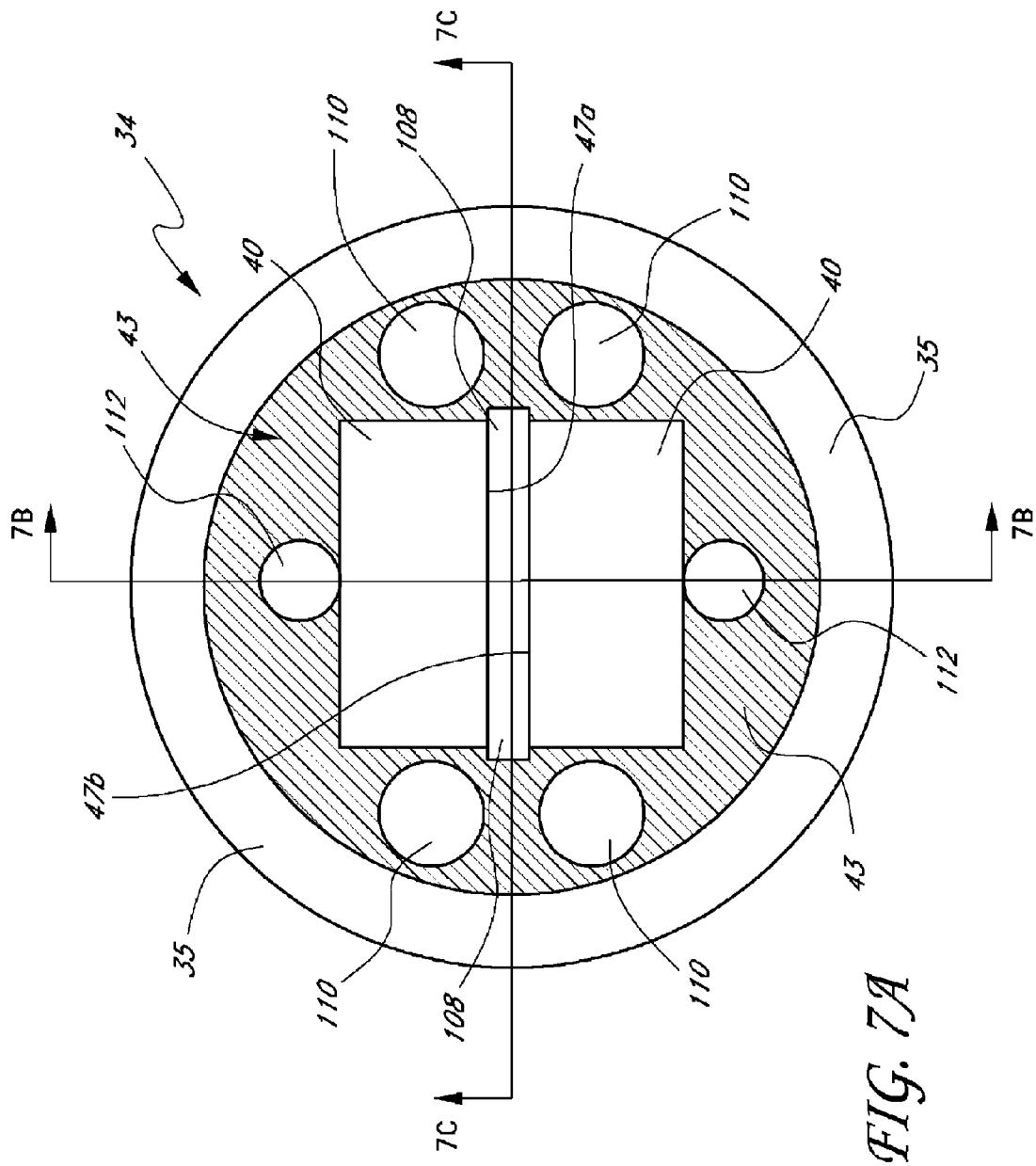
FIG. 7A is a schematic illustration of the ultrasound assembly of FIG. 5 housed within the inner core of FIG. 4.

FIG. 7A illustrates one preferred technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

Referring still to FIG. 7A, the common wire 108 comprises an elongate, flat piece of electrically conductive material in electrical contact with a pair of ultrasound radiating members 40. The pair of ultrasound radiating members 40 includes a first transducer with a first face 47a and a second transducer with a second face 47b. The transducers are arranged in a way that the first face 47a of the first transducer and the second face 47b of the second transducer face each other, and are in contact with the common wire 108. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. Lead wires 110 are preferably separated from the other components of the ultrasound assembly 42, thus preventing interference with the operation of the ultrasound radiating members 40 as described above. For example, in one preferred embodiment, the inner core 34 is filled with an insulating potting material 43, thus deterring unwanted electrical contact between the various components of the ultrasound assembly 42.

FIGS. 7B and 7C illustrate cross sectional views of the inner core 34 of FIG. 7A taken along lines 7B-7B and 7C-7C, respectively. As illustrated in FIG. 7B, the ultrasound radiating members 40 are mounted in pairs along the common wire 108. The first ultrasound radiating member has a first face 47a that is facing a second face 47b of the second ultrasound radiating member. The ultrasound radiating members 40 are connected by positive contact wires 112, such that substantially the same voltage is applied to each ultrasound radiating member 40. As illustrated in FIG. 7C, the common wire 108 preferably comprises wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

Figure 7D:
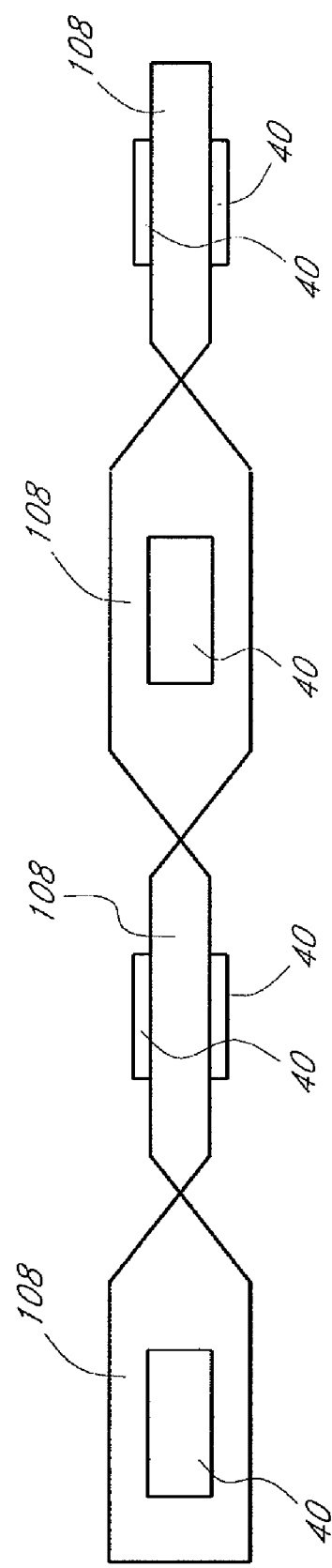
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

One of ordinary skill in the art will recognize that the wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focused, more diffuse ultrasonic energy field to the treatment site.

In a preferred embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configuration may be used. For example, disc-shaped ultrasound radiating members 40 can be used in other embodiments. In a preferred embodiment, the common wire 108 comprises copper, and is about 0.005 inches thick, although other electrically conductive materials and other dimensions can be used in other embodiments. Lead wires 110 are preferably 36 gauge electrical conductors, while positive contact wires 112 are preferably 42 gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment 1 MHz and 3 MHz. In yet another embodiment, the ultrasound radiating members 40 are operated with a frequency of about 2 MHz.

Figure 8:
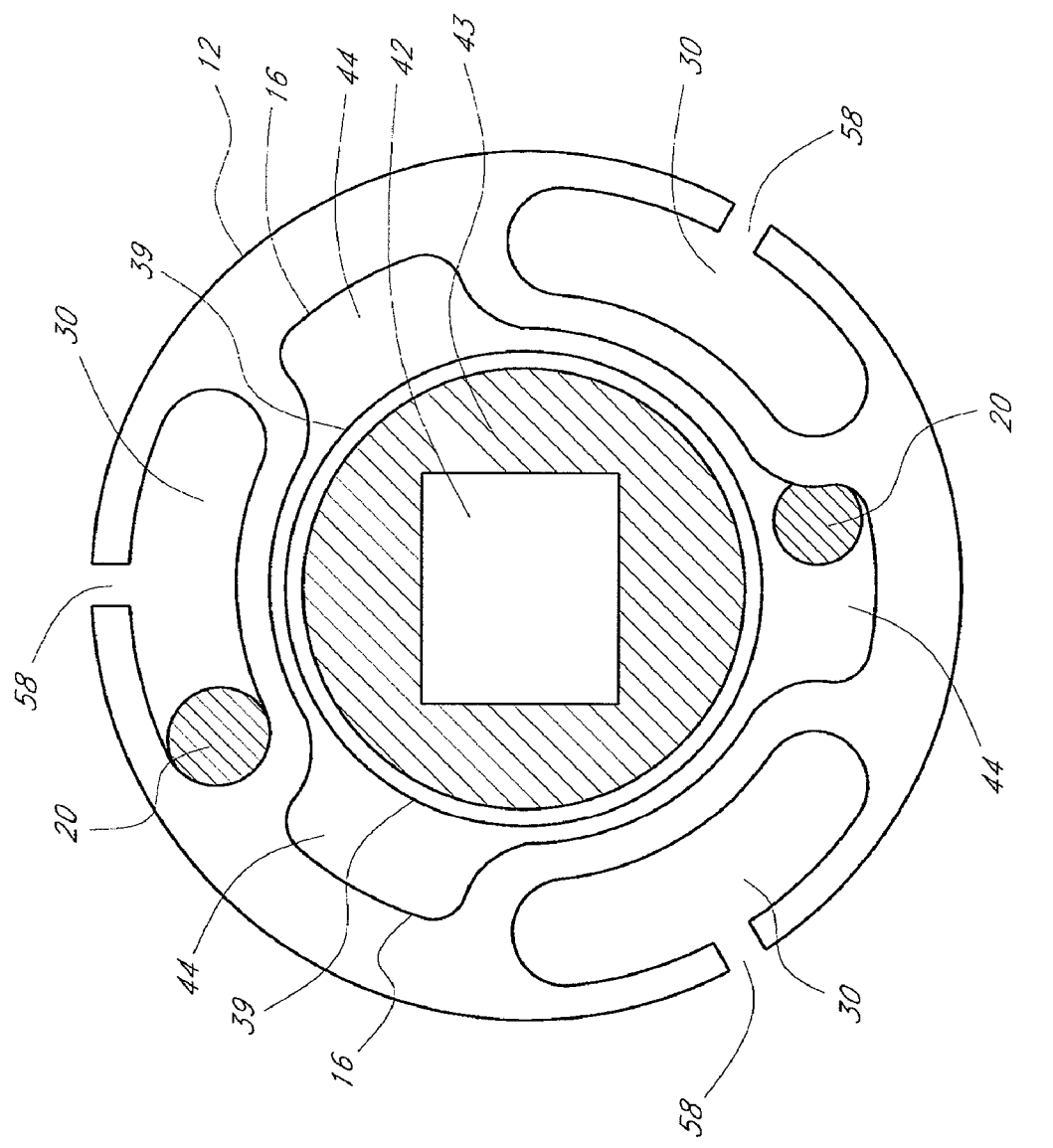
FIG. 8 illustrates the energy delivery section of the inner core of FIG. 4 positioned within the energy delivery section of the tubular body of FIG. 2.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in a preferred embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. Thus, a source of therapeutic compound coupled to the inlet port 32 provides a hydraulic pressure which drives the therapeutic compound through the fluid delivery lumens 30 and out the fluid delivery ports 58.

By evenly spacing the fluid delivery lumens 30 around the circumference of the tubular body 12, as illustrated in FIG. 8, a substantially even flow of therapeutic compound around the circumference of the tubular body 12 can be achieved. In addition, the size, location and geometry of the fluid delivery ports 58 can be selected to provide uniform fluid flow from the fluid delivery ports 30 to the treatment site. For example, in one embodiment, fluid delivery ports closer to the proximal region of the energy delivery section 18 have smaller diameters then fluid delivery closer to the distal region of the energy delivery section 18, thereby allowing uniform delivery of fluid across the entire energy delivery section.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to 0.0020 inches in the distal region of the energy delivery section 18. The increase in size between adjacent fluid delivery ports 58 depends on the material comprising the tubular body 12, and on the size of the fluid delivery lumen 30. The fluid delivery ports 58 can be created in the tubular body 12 by punching, drilling, burning or ablating (such as with a laser), or by any other suitable method. Therapeutic compound flow along the length of the tubular body 12 can also be increased by increasing the density of the fluid delivery ports 58 toward the distal region 15 of the tubular body 12.

It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid can is introduced through the proximal access port 31 such that cooling fluid flow is produced through cooling fluid lumens 44 and out distal exit port 29 (see FIG. 1). The cooling fluid lumens 44 are preferably evenly spaced around the circumference of the tubular body 12 (that is, at approximately 120 degree increments for a three-lumen configuration), thereby providing uniform cooling fluid flow over the inner core 34. Such a configuration is desirably to remove unwanted thermal energy at the treatment site. As will be explained below, the flow rate of the cooling fluid and the power to the ultrasound assembly 42 can be adjusted to maintain the temp of the inner core energy delivery section 41 within a desired range.

In a preferred embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, the inner core outer body 35 preferably comprises a material having the ability to transmit torque. Suitable materials for the inner core outer body 35 include, but are not limited to, polyimides, polyesters, polyurethanes, thermoplastic elastomers and braided polyimides.

In a preferred embodiment, the fluid delivery lumens 30 and the cooling fluid lumens 44 are open at the distal end of the tubular body 12, thereby allowing the therapeutic compound and the cooling fluid to pass into the patient's vasculature at the distal exit port. Or, if desired, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can prevented from passing through the distal exit port by making providing the inner core 34 with a length that is less than the length of the tubular body. In other embodiments, a protrusion is formed on the internal side of the tubular body in the distal region 15, thereby preventing the inner core 34 from passing through the distal exit port.

In still other embodiments, the catheter 10 further comprises an occlusion device (not shown) positioned at the distal exit port 29. The occlusion device preferably has a reduced inner diameter that can accommodate a guidewire, but that is less than the inner diameter of the central lumen 51. Thus, the inner core 34 is prevented from extending through the occlusion device and out the distal exit port 29. For example, suitable inner diameters for the occlusion device include, but are not limited to, about 0.005 inches to about 0.050 inches. In other embodiments, the occlusion device has a closed end, thus preventing cooling fluid from leaving the catheter 10, and instead recirculating to the proximal region 14 of the tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 8, the tubular body 12 further comprises one or more temperature sensors 20, which are preferably located within the energy delivery section 18. In such embodiments, the proximal region 14 of the tubular body 12 includes a temperature sensor lead which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30 (as illustrated), and/or within one or more of the cooling fluid lumens 44.

Figure 9:
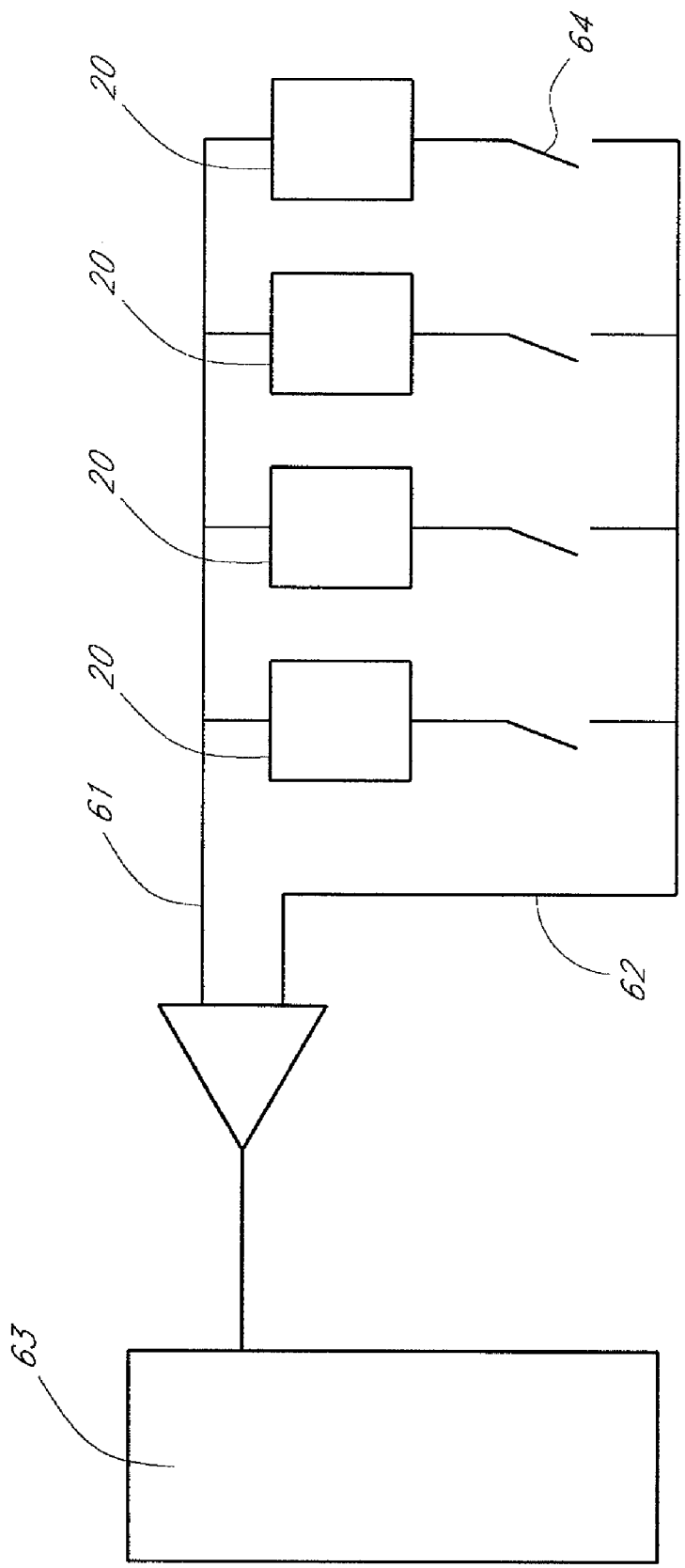
FIG. 9 illustrates a wiring diagram for connecting a plurality of temperature sensors with a common wire.

FIG. 9 illustrates one embodiment for electrically connecting the temperature sensors 20. In such embodiments, each temperature sensor 20 is coupled to a common wire 61 and is associated with an individual return wire 62. Accordingly, n+1 wires can be used to independently sense the temperature at n distinct temperature sensors 20. The temperature at a particular temperature sensor 20 can be determined by closing a switch 64 to complete a circuit between that thermocouple's individual return wire 62 and the common wire 61. In embodiments wherein the temperature sensors 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2n wires through the tubular body 12 to independently sense the temperature at n independent temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
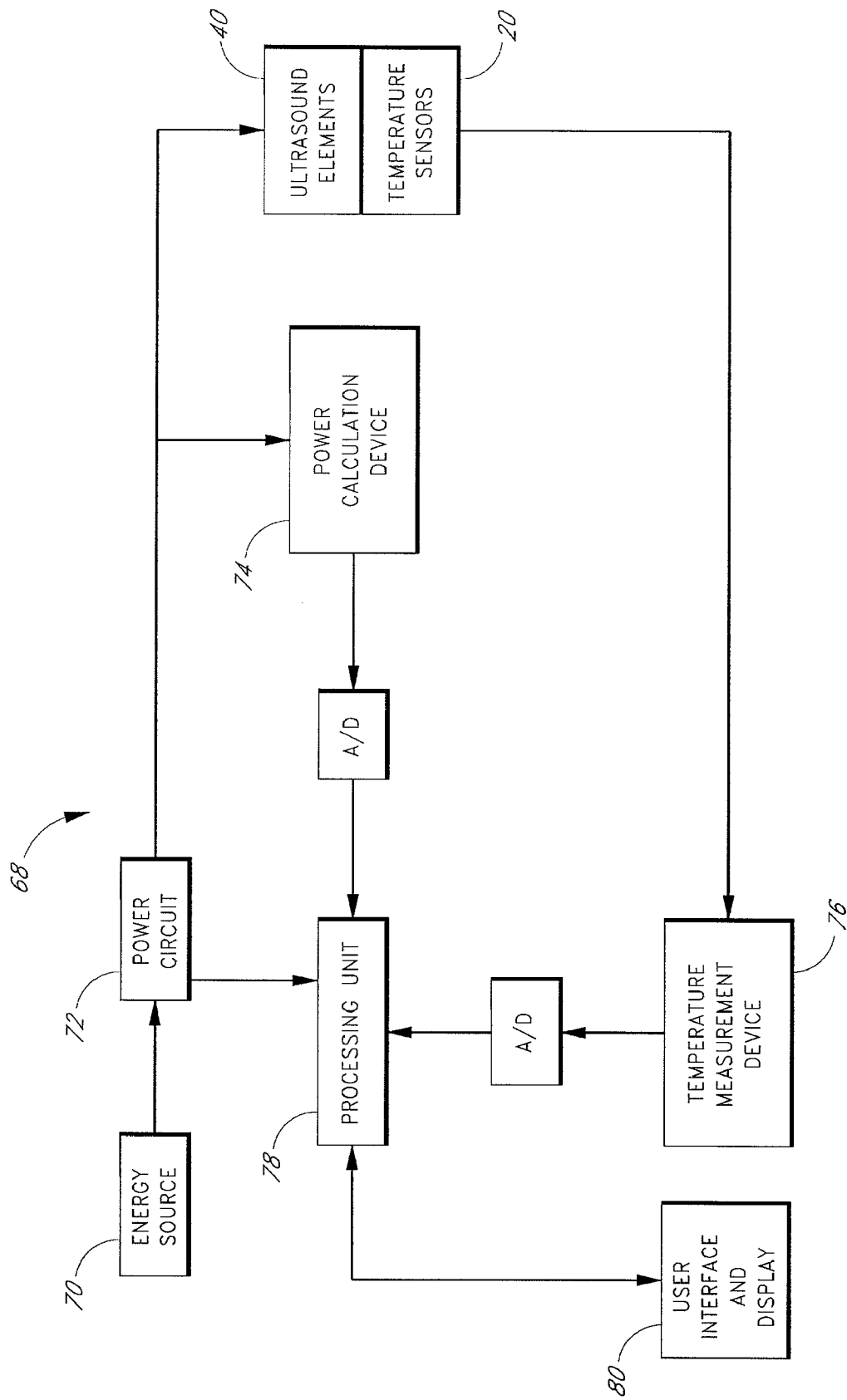
FIG. 10 is a block diagram of a feedback control system for use with an ultrasonic catheter.

FIG. 10 illustrates one embodiment of a feedback control system 68 that can be used with the catheter 10. The feedback control system 68 can be integrated into the control system that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

The feedback control system 68 preferably comprises an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In operation, the temperature at each temperature sensor 20 is determined by the temperature measurement device 76. The processing unit 78 receives each determined temperature from the temperature measurement device 76. The determined temperature can then be displayed to the user at the user interface and display 80.

The processing unit 78 comprises logic for generating a temperature control signal. The temperature control signal is proportional to the difference between the measured temperature and a desired temperature. The desired temperature can be determined by the user (at set at the user interface and display 80) or can be preset within the processing unit 78.

The temperature control signal is received by the power circuits 72. The power circuits 72 are preferably configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is preferably reduced in response to that temperature control signal. Similarly, when the temperature control signal is below a particular level, the power supplied to a particular group of ultrasound radiating members 40 is preferably increased in response to that temperature control signal. After each power adjustment, the processing unit 78 preferably monitors the temperature sensors 20 and produces another temperature control signal which is received by the power circuits 72.

The processing unit 78 preferably further comprises safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating member 40 can be identically adjusted in certain embodiments. In a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 also receives a power signal from a power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, it is generally desirable to prevent tissue at a treatment site from increasing more than 6 degrees C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as for example a computer with software. When the processing unit 78 is a computer it can include a central processing unit ("CPU") coupled through a system bus. As is well known in the art, the user interface and display 80 can comprise a mouse, a keyboard, a disk drive, a display monitor, a nonvolatile memory system, or any another. Also preferably coupled to the bus is a program memory and a data memory.

In lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 can then be adjusted according to the preset profiles.

The ultrasound radiating members are preferably operated in a pulsed mode. For example, in one embodiment, the time average power supplied to the ultrasound radiating members is preferably between about 0.1 watts and 2 watts and more preferably between about 0.5 watts and 1.5 watts. In certain preferred embodiments, the time average power is approximately 0.6 watts or 1.2 watts. The duty cycle is preferably between about 1% and 50% and more preferably between about 5% and 25%. In certain preferred embodiments, the duty ratio is approximately 7.5% or 15%. The pulse averaged power is preferably between about 0.1 watts and 20 watts and more preferably between approximately 5 watts and 20 watts. In certain preferred embodiments, the pulse averaged power is approximately 8 watts and 16 watts. The amplitude during each pulse can be constant or varied.

In one embodiment, the pulse repetition rate is preferably between about 5 Hz and 150 Hz and more preferably between about 10 Hz and 50 Hz. In certain preferred embodiments, the pulse repetition rate is approximately 30 Hz. The pulse duration is preferably between about 1 millisecond and 50 milliseconds and more preferably between about 1 millisecond and 25 milliseconds. In certain preferred embodiments, the pulse duration is approximately 2.5 milliseconds or 5 milliseconds.

In one particular embodiment, the transducers are operated at an average power of approximately 0.6 watts, a duty cycle of approximately 7.5%, a pulse repetition rate of 30 Hz, a pulse average electrical power of approximately 8 watts and a pulse duration of approximately 2.5 milliseconds.

The ultrasound radiating member used with the electrical parameters described herein preferably has an acoustic efficiency greater than 50% and more preferably greater than 75%. The ultrasound radiating member can be formed a variety of shapes, such as, cylindrical (solid or hollow), flat, bar, triangular, and the like. The length of the ultrasound radiating member is preferably between about 0.1 cm and about 0.5 cm. The thickness or diameter of the ultrasound radiating members is preferably between about 0.02 cm and about 0.2 cm.

Figure 11A:
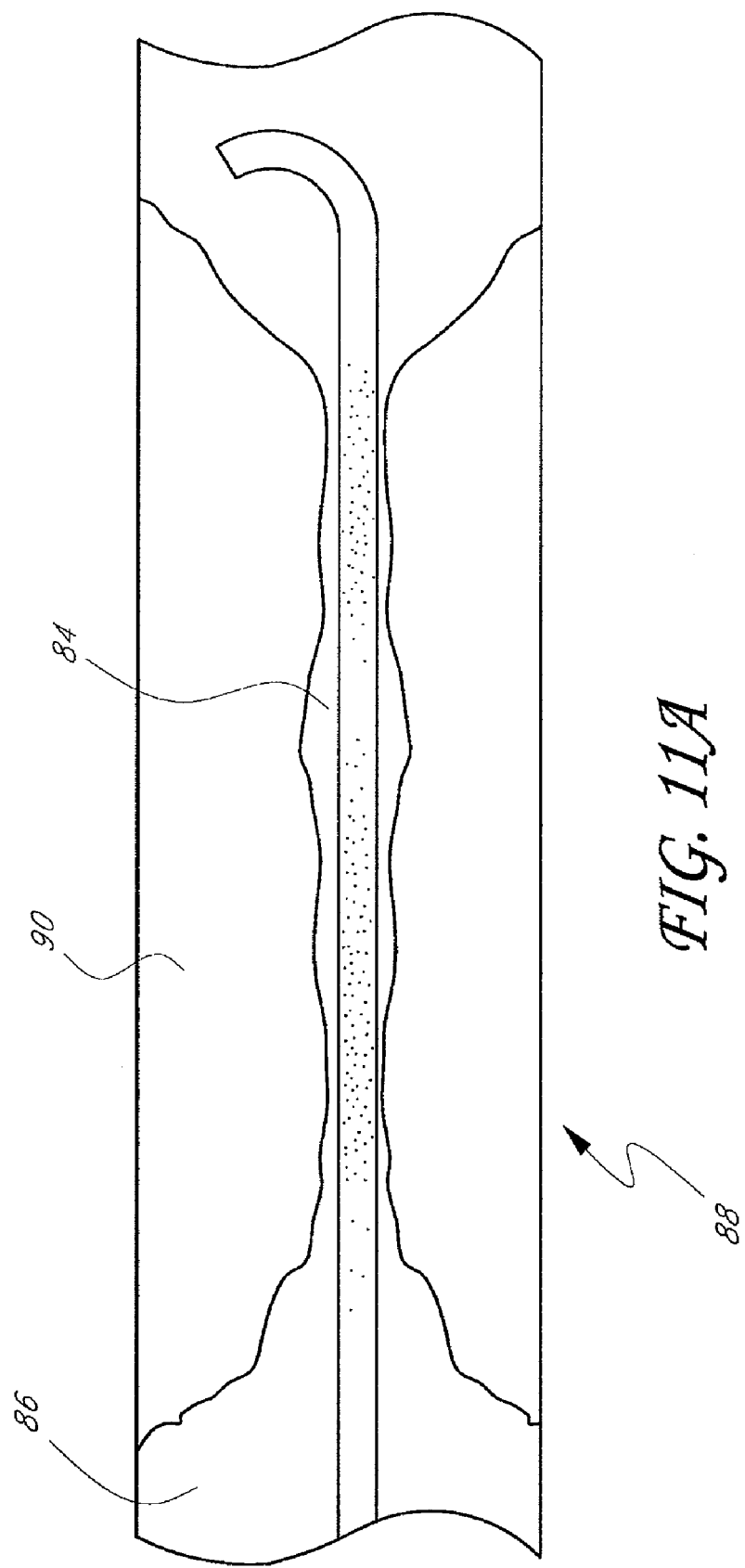
FIG. 11A is a side view of a treatment site.

FIGS. 11A through 11D illustrate a method for using the ultrasonic catheter 10. As illustrated in FIG. 11A, a guidewire 84 similar to a guidewire used in typical angioplasty procedures is directed through a patient's vessels 86 to a treatment site 88 which includes a clot 90. The guidewire 84 is directed through the clot 90. Suitable vessels 86 include, but are not limited to, the large periphery blood vessels of the body. Additionally, as mentioned above, the ultrasonic catheter 10 also has utility in various imaging applications or in applications for treating and/or diagnosing other diseases in other body parts.

As illustrated in FIG. 11B, the tubular body 12 is slid over and is advanced along the guidewire 84 using conventional over-the-guidewire techniques. The tubular body 12 is advanced until the energy delivery section 18 of the tubular body 12 is positioned at the clot 90. In certain embodiments, radiopaque markers (not shown) are positioned along the energy delivery section 18 of the tubular body 12 to aid in the positioning of the tubular body 12 within the treatment site 88.

Figure 11C:
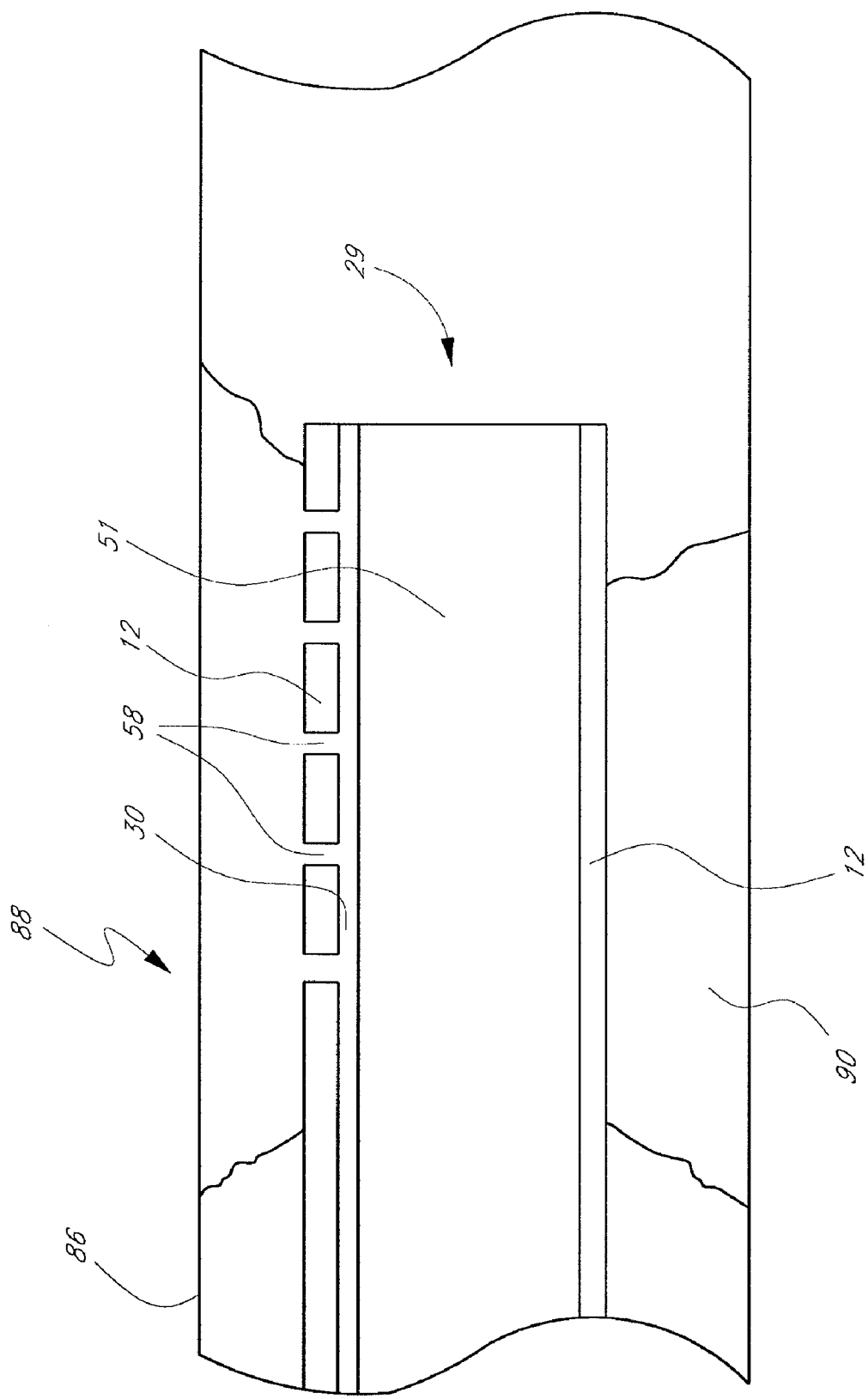
FIG. 11C is a cross-sectional view of the distal end of the ultrasonic catheter of FIG. 11B positioned at the treatment site before a treatment.

As illustrated in FIG. 11C, the guidewire 84 is then withdrawn from the tubular body 12 by pulling the guidewire 84 from the proximal region 14 of the catheter 10 while holding the tubular body 12 stationary. This leaves the tubular body 12 positioned at the treatment site 88.

Figure 11D:
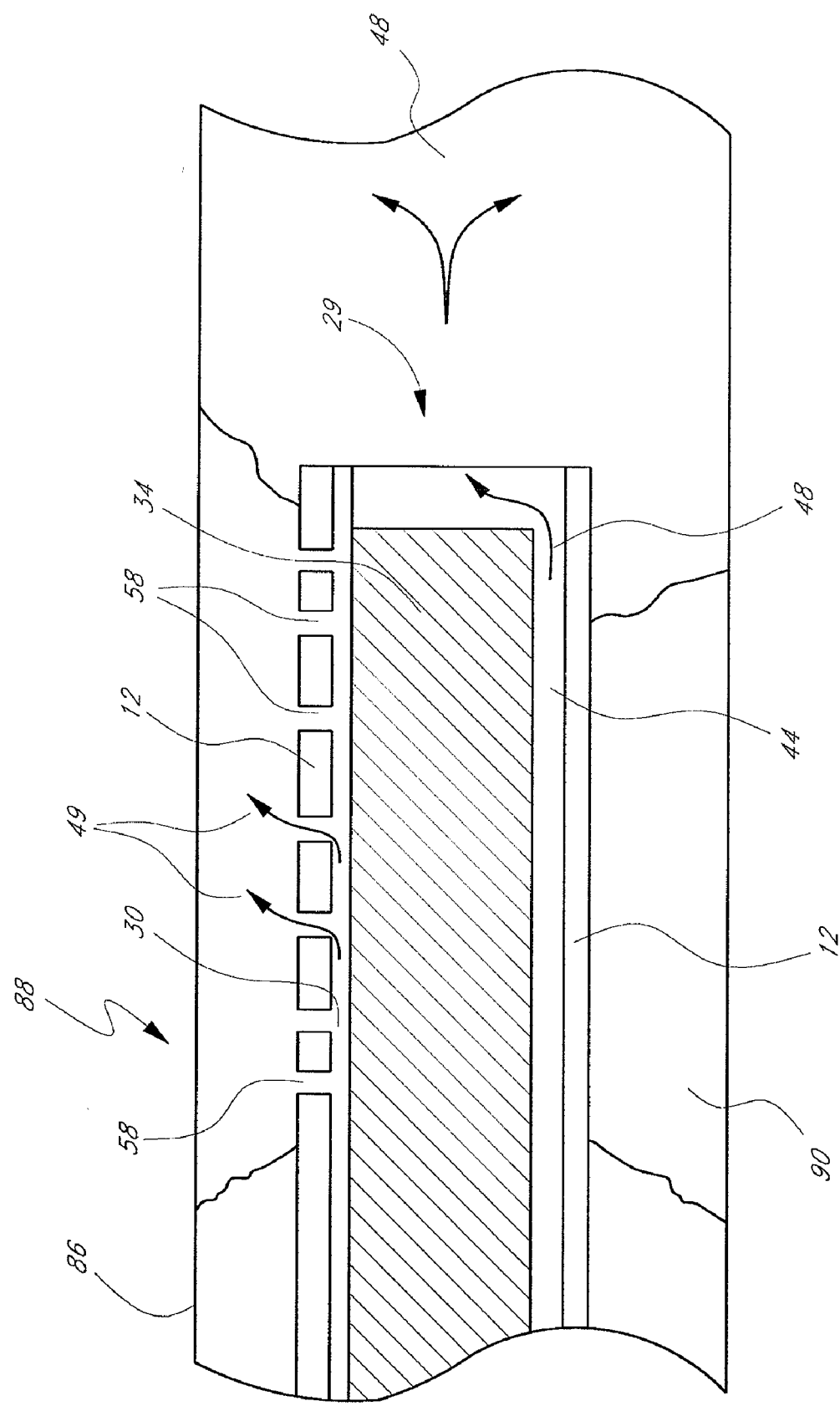
FIG. 11D is a cross-sectional view of the distal end of the ultrasonic catheter of FIG. 11C, wherein an inner core has been inserted into the tubular body to perform a treatment.

As illustrated in FIG. 11D, the inner core 34 is then inserted into the tubular body 12 until the ultrasound assembly 42 abuts against the occlusion device and is positioned at least partially within the energy delivery section 18 of the tubular body 12. Once the inner core 34 is properly positioned, the ultrasound assembly 42 is activated to deliver ultrasonic energy through the energy delivery section 18 to the clot 90. As described above, suitable ultrasonic energy is delivered with a frequency between about 20 kHz and about 20 MHz.

In a certain embodiment, the ultrasound assembly 42 comprises sixty ultrasound radiating members 40 (comprising 30 ultrasound elements) spaced over a length of approximately 30 to 50 cm. In such embodiments, the catheter 10 can be used to treat an elongate clot 90 without requiring movement of or repositioning of the catheter 10 during the treatment. However, it will be appreciated that in modified embodiments the inner core 34 can be moved or rotated within the tubular body 12 during the treatment. Such movement can be accomplished by maneuvering the proximal hub 37 of the inner core 34 while holding the backend hub 33 stationary.

Referring again to FIG. 11D, arrows 48 indicate that a cooling fluid flows through the cooling fluid lumen 44 and out the distal exit port 29. Likewise, arrows 49 indicated that a therapeutic compound flows through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Consequently, the steps illustrated in FIGS. 11A through 11D can be performed in a variety of different orders than that described above. The therapeutic compound and ultrasonic energy are preferably applied until the clot 90 is partially or entirely dissolved. Once the clot 90 has been dissolved to the desired degree, the tubular body 12 and the inner core 34 are withdrawn from the treatment site 88.

Figure 12:
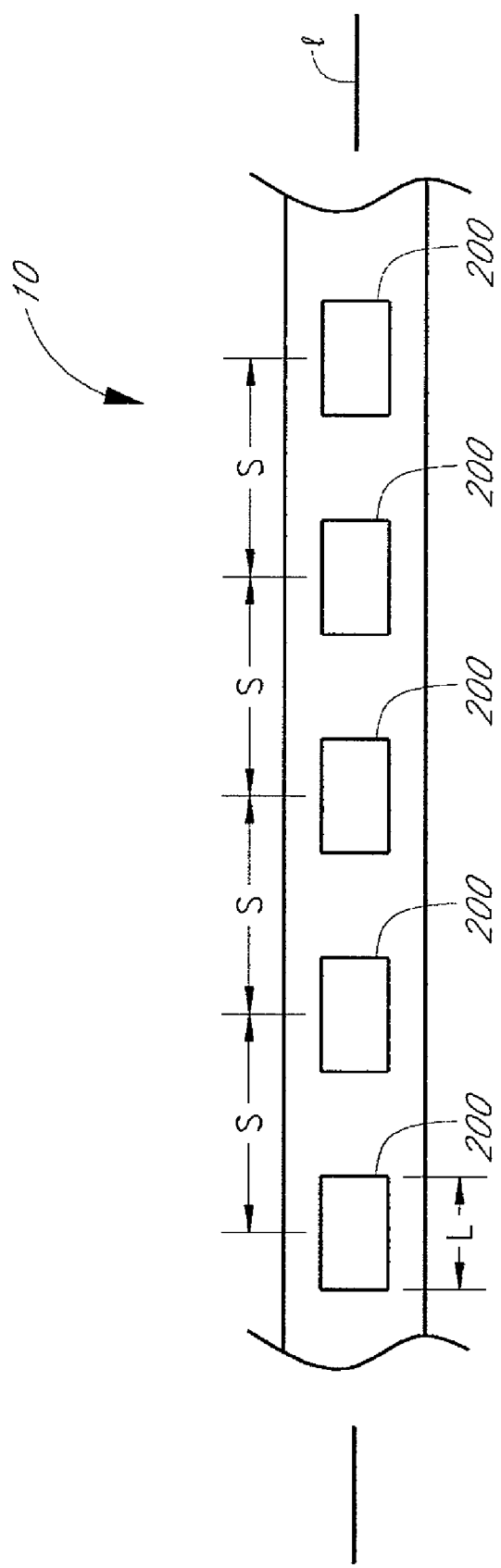
FIG. 12 is a schematic illustration of the spacing between ultrasonic elements within an ultrasonic catheter.

With reference now to FIG. 12, the physical spacing of the ultrasound elements 200 in the catheter 10 according to one embodiment will now be described. As shown in FIG. 12, with respect to the longitudinal direction I of the catheter 10, each element 200 has a longitudinal length L. In addition, there is a longitudinal spacing S between each of the ultrasound elements 20 as measured between the longitudinal center of longitudinally adjacent elements 20. As mentioned above, in one embodiment, the length L of the a ultrasound radiating member 40 (not shown) is preferably between about 0.1 cm and about 0.5 cm. The thickness or diameter of the ultrasound radiating members 40 in one embodiment is between about 0.02 cm and about 0.2 cm. The elements are operated at an average power (typically measured in Watts). Depending upon the configuration, the elements can be operated between at an average of about 0.2-0.9 W per element.

The spacing S between the ultrasound elements 20 is preferably selected to enhance bioefficacy (e.g., enhancing lysis in the presence of a drug) while balancing the design concerns that decreasing the spacing S between the ultrasound elements (e.g., by increasing the longitudinal density of the elements) can increase the cost of the catheter and/or decrease the flexibility of the catheter.

Applicant has discovered that the spacing S between elements has surprising consequences. For examples, tests were preformed on a three catheters having a spacing S between elements of 0.5 cm 1.0 cm and 1.7 cm respectively. In the tests, the catheters were tested for their bioefficacy (eg., lysis enhancement by ultrasound in combination with a drug). It was theorized that for the same average power decreasing the spacing S between elements would produce increased bioefficacy due to the higher local energy delivery from the closer spacing. However, as indicated in Table A below, the difference between 0.5 cm and 1.0 cm spacing is statistically insignificant. It is theorized that may be because the effect of local energy delivery reaches a plateau after which there is no or little further lysis enhancement. For example, as shown in Table B, when the average power is reduced (e.g., 0.45 W to 0.30 W) the theorized plateau effect has not been reached and there is a benefit to decreasing the spacing (e.g., from 1 cm to 0.5 cm) between elements.

TABLE A

Power per Element .45 W

| Spacing (cm) | W/cm | Average % Clot Reduction |
|---|---|---|
| 0.5 | .9 | 63.97 ± 1.99% |
| 1.0 | .45 | 62.80 ± 2.69% |
| 1.7 | .26 | 57.82 ± 3.62% |

TABLE B

Power per Element .30 W

| Spacing (cm) | W/cm | Average % Clot Reduction |
|---|---|---|
| 0.5 | .6 | 63.98 ± 3.91% |
| 1.0 | .3 | 60.08 ± 3.12% |

It is theorized that the plateau is related to the linear density of the power applied to the treatment cite. In one preferred embodiment, the spacing S between elements and the power per element is selected such that the longitudinal linear power density is between about 0.2 and about 1.0 W/cm. In another embodiment, the longitudinal linear power density is between about 0.3 and 0.6 W/cm. In another embodiment, the longitudinal linear power density is between about 0.4 and about 0.5 W/cm and yet another embodiment the longitudinal linear power is about 0.45 W/cm.

With respect to the catheter embodiments illustrated and described above, in one embodiment, the catheter comprises 5 groups of ultrasonic elements where each group comprises 6 ultrasonic pairs or elements (see e.g., FIGS. 5 and 6). For a catheter with a treatment length of, for example, 30 cm operating at a power of about 0.45 W per element it would be advantageous to have the elements spaced 1.0 cm apart. For catheters with larger treatment lengths (e.g., 40 cm and 50 cm), the results described above would indicate that the spacing between elements should be maintained at about 1.0 cm to enhance bioefficacy. The spacing S can be maintained at about 1.0 cm by increasing the number of elements per group and/or increasing the number of groups. For treatment lengths less than 30 cm (e.g., 20 cm, 10 cm), the spacing S can be maintained at about 1 cm by decreasing the number of groups, and/or decreasing the number of ultrasonic elements per group. If the operating power is less or greater than about 0.45 W, the spacing S between elements can be adjusted as described above to maintain the desired linear power density.

It should be appreciated that the parameters and methods related to spacing S are not limited to the catheter embodiments disclosed herein. Those of skill in the art will recognize that the parameters and methods can be applied to catheters that due not utilize a separate drug deliver catheter and an core member or include additional members. In addition, ultrasonic elements of different configurations (e.g., cylindrical, cubic, etc.) can be used. That is, the ultrasound element need not comprise two rectangular elements as described herein. Moreover, in certain configurations, it may be advantageous that the spacing S between elements are not equal but vary along the length of the catheter. In still other embodiments, the catheter can be configured to treat treatment sites with lengths less than e.g., 10 cm. In such embodiments, the catheter may comprise less than, for example, 10 ultrasound elements. In some embodiments, the catheter may comprise only 1-5 ultrasound elements.

The linear density described above can be applied to catheters configured for long segment peripheral arterial occlusions, such as those in the arteries of the leg, may have an axial length in the range of 10 to 50 cm as described above. The linear density can also be applied to shorter occlusions in the same of different parts of the body. For example, the linear density can be applied to a catheter configured for treating clots in the brain.

While the foregoing detailed description has described several embodiments of the apparatus and methods of the present invention, it is to be understood that the above description is illustrative only and not limited of the disclosed invention. It will be appreciated that the specific dimensions of the various catheters and inner cores can differ from those described above, and that the methods described can be used within any biological conduit in a patient's body, while remaining within the scope of the present invention. Thus, the present invention is to be limited only by the claims that follow.

What is claimed is:

1. A catheter system for delivering ultrasonic energy to a treatment site, the catheter system comprising: a tubular body having a proximal end, a distal end and a treatment zone located between the distal end and the proximal end; and a plurality of ultrasonic assemblies configured to be positioned within the treatment zone; each of the ultrasonic assemblies comprising a plurality of ultrasound elements forming a treatment length, each ultrasound element having a longitudinal length and a longitudinal spacing between longitudinal centers of longitudinally adjacent ultrasound elements, wherein the ultrasound assembly is configured such that the average power supplied between any two ultrasound elements in the treatment zone has a longitudinal density between about 0.2 and about 1.0 W/cm and wherein each ultrasound assembly has a different treatment length.

2. The catheter system of claim 1, further comprising a therapeutic compound delivery lumen that extends through the tubular body and terminates in at least one outlet positioned in the treatment zone.

3. The catheter system of claim 1 wherein each of the ultrasonic assembly is positioned within an inner core.

4. The catheter system of claim 3, wherein the inner core can be removably inserted into the tubular body so as to position the ultrasonic assembly in the treatment zone.

5. The catheter system of claim 1, wherein the plurality of ultrasound elements are electrically coupled to a first wire and a second wire.

6. The catheter system of claim 5, further comprising a control system configured such that a voltage can be applied simultaneously across the first and second wires to drive the plurality of ultrasound elements.

7. The catheter system of claim 1, wherein the treatment zone has a greater acoustic transparency than a proximal region of the tubular body.

8. The catheter system of claim 1, wherein each ultrasound assembly comprises a plurality of ultrasound transducer pairs, each ultrasound transducer pair comprising a first transducer with a first face and a second transducer with a second face, the first face of the first transducer and the second face of the second transducer facing each other.

9. The catheter system of claim 1, wherein the longitudinal density is between about 0.3 and about 0.6 W/cm.

10. The catheter system of claim 1, wherein the longitudinal density is between about 0.4 and about 0.5 W/cm.

11. A catheter system for delivering ultrasonic energy and a therapeutic compound to a treatment site within a body lumen, the catheter system comprising:
  a tubular body having a proximal end, a distal end and an energy delivery section positioned between the proximal end and the distal end, wherein the energy delivery section has a length greater than about 10 cm;
  a fluid delivery lumen extending at least partially through the tubular body and having at least one outlet in the energy delivery section;
  a plurality of ultrasound assemblies, each comprising;
    an inner core configured for insertion into the tubular body, the inner core comprising a plurality of ultrasound radiating elements to be positioned within the energy delivery section and form a treatment length;
    each ultrasound radiating element having a longitudinal length and a longitudinal spacing between longitudinal centers of longitudinally adjacent ultrasound radiating elements;
    the catheter system supplies an average power between any two ultrasound radiating elements in the energy delivery section so that the catheter has a longitudinal power density between about 0.3 and about 0.6 W/cm within the treatment length; and
  each of the plurality of ultrasound assemblies has a different treatment length.

12. The catheter system of claim 11, wherein the fluid delivery lumen comprises a plurality of lumens formed within the tubular body.

13. The catheter system of claim 11, wherein the plurality of ultrasound radiating elements are electrically coupled into a plurality of electrical groups, each group of ultrasound radiating members independently drivable by a control system.

14. The catheter system of claim 13, wherein the ultrasound radiating members are allocated into at least five electrical groups.

15. The catheter system of claim 11, wherein the ultrasonic radiating elements comprise ultrasonic transducers in the shape of a rectangular bar.

16. The catheter system of claim 11, wherein the longitudinal spacing between ultrasound elements is about 1.0 cm.

* * * * *